United States Patent
Kumar et al.

(10) Patent No.: US 8,005,691 B2
(45) Date of Patent: *Aug. 23, 2011

(54) SYSTEM AND METHOD FOR COMMUNICATING PHYSIOLOGICAL DATA OVER A WIDE AREA NETWORK

(75) Inventors: Kishore Kumar, San Jose, CA (US); Laxmikant Rashinkar, Fremont, CA (US)

(73) Assignee: Televital, Inc., San Jose, CA (US)

( * ) Notice: Subject to any disclaimer, the term of this patent is extended or adjusted under 35 U.S.C. 154(b) by 860 days.

This patent is subject to a terminal disclaimer.

(21) Appl. No.: 11/668,399

(22) Filed: Jan. 29, 2007

(65) Prior Publication Data

US 2007/0130287 A1    Jun. 7, 2007

Related U.S. Application Data

(63) Continuation of application No. 10/109,958, filed on Mar. 28, 2002, now Pat. No. 7,188,151.

(60) Provisional application No. 60/279,562, filed on Mar. 28, 2001.

(51) Int. Cl.
*G06F 19/00*    (2006.01)

(52) U.S. Cl. .................................................. 705/3
(58) Field of Classification Search .................. 705/2, 4; 600/300; 128/670; 709/206, 230; 607/59
See application file for complete search history.

(56) References Cited

U.S. PATENT DOCUMENTS

| | | | | |
|---|---|---|---|---|
| 5,441,047 A * | 8/1995 | David et al. | ................... | 600/483 |
| 5,987,519 A * | 11/1999 | Peifer et al. | ................... | 709/230 |
| 6,364,834 B1 * | 4/2002 | Reuss et al. | ................... | 600/300 |
| 6,424,996 B1 * | 7/2002 | Killcommons et al. | ...... | 709/206 |
| 6,442,432 B2 * | 8/2002 | Lee | ................................ | 607/59 |

* cited by examiner

*Primary Examiner* — Gerald J. O'Connor
*Assistant Examiner* — John A Pauls
(74) *Attorney, Agent, or Firm* — Zilka-Kotab, PC

(57) ABSTRACT

A system and method are provided for network-based monitoring of physiological data. At least one patient-side device collects physiological data from a patient. A provider-side device receives the data from at least one patient-side device via a wide area network. An engine communicates with at least one patient-side device and the provider-side device. The engine manages transmission of the data from the patient-side device to the provider-side device.

6 Claims, 27 Drawing Sheets

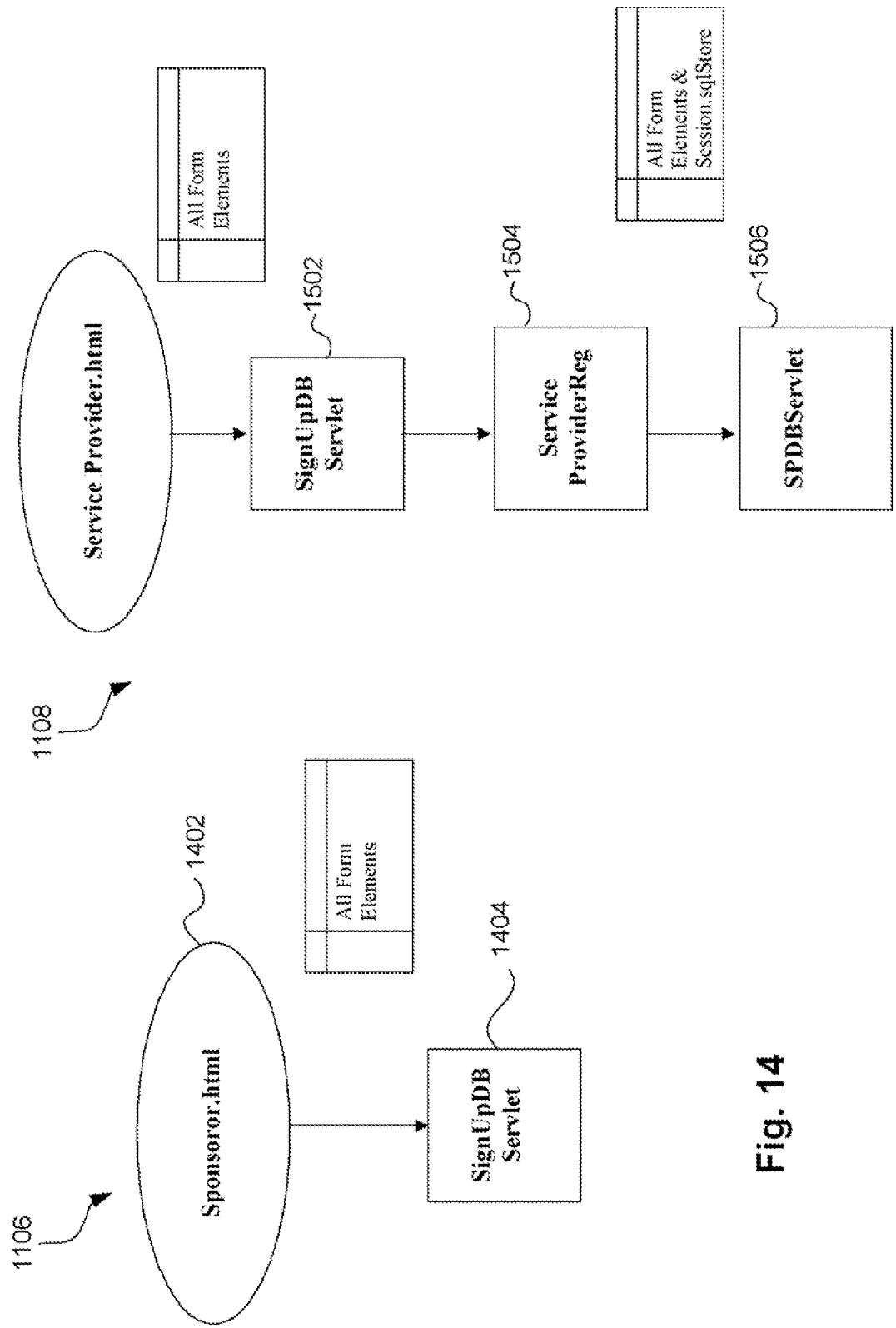

SYSTEM AND METHOD FOR COMMUNICATING PHYSIOLOGICAL DATA OVER A WIDE AREA NETWORK

PRIOR APPLICATIONS

This application is a continuation of U.S. patient application Ser. No. 10/109,958 filed Mar. 28, 2002 now U.S. Pat. No. 7,188,151, and also claims priority from Provisional U.S. patent application entitled System and Method for Secure Internet Device Monitoring, filed Mar. 28, 2001 under Ser. No. 60/279,562, and which are both incorporated herein by reference for all purposes.

FIELD OF THE INVENTION

The present invention relates to remote monitoring of devices over a wide area network, and more particularly, this invention relates to network-based transmission of data from a physiological collecting device.

BACKGROUND OF THE INVENTION

Telemedicine, also known as telehealth, is the communication over distance through text, audio or video media for the education, evaluation and treatment of disease and illness. Telehealth is the use of information technology and telecommunication for providing access to health assessments, diagnoses, interventions, supervision, consultations, education, and information across a distance.

One prior art telehealth system includes biofeedback applications provided by Floan, James, Earles and Andrasik, and the U.S. Military which uses two telephone lines combined with other technology to conduct biofeedback sessions over great distances. The military application uses two way audio and video (teleconferencing) to communicate along with PC Anywhere type programs for PC to PC communication; but does not allow for the real-time transfer and observation of the physiological signals.

Disease management companies, so far are not providing real-time transmission of physiological data. The information that they do collect like EKG, and blood pressure are recorded and sent to the doctor hours later.

There is a great need for telemedicine technologies in homecare and ambulatory settings as outpatient disease management handles roughly one hundred million chronic patients in the US alone, which costs millions of dollars each year in ER, hospital, specialty and primary care.

It would therefore be desirable to provide an internet abased software system capable of streaming, in real-time, EMG, ECG, EEG, peripheral temp, respiration, skin conductance/resistance, heart-rate variability, FFT, and DFT that would be capable of supporting most hardware.

It would also be desirable to provide such a system in which the hardware is plug-and-play compatible and thus will not require anyone to install any extra software.

What is also needed is software that can transmit signals in real-time, while simultaneously sorting the data so that as the session is being recorded a user could back-up to see past events.

DISCLOSURE OF THE INVENTION

The present invention provides a system and method for remote monitoring of medical and/or biofeedback devices over a wide area network (WAN) such as the Internet. In a preferred embodiment, a browser-based engine supports real-time streaming of information over the WAN. In an exemplary embodiment, the system allows for the real-time streaming of raw, interpreted, and processed physiological data as well as textual/audio/video data from a patient/client to a health care provider. However, other embodiments may contemplate non-medical/non-biofeedback devices and non-human monitoring.

The system of the exemplary embodiment preferably includes at least one patient-side device for collecting data from a patient/client, a provider-side device, and an engine, each coupled to the WAN. The engine manages transmission of the data from the patient-side device to the provider-side device. This means that the engine may configure the devices to transfer the data directly from one device to the other; may receive the data from the patient-side device and transmit the raw or processed data to the provider-side device; may store the data for later transmission to the provider-side device, etc.

The embodiments presented herein contemplate connection of multiple patient-side devices, provider-side devices, and engines. Because a plurality of devices and engines may be in operation, the system may be capable of networking the numerous devices and/or engines into individual, group, clinic, hospital, or other electronic record systems.

For simplicity, the discussion will proceed with description of a system having a single patient-side and provider-side device. The patient-side device is located with the patient/client and gathers physiological data from the patient/client. The patient-side device can include, for example, a medical and/or biofeedback device that communicates through a serial, parallel, wireless, or customized interface. The patient-side device may then be connected via a computing device, such as a computer, personal digital assistant (PDA), etc., to the WAN. Alternatively, the patient-side device may have a built-in computing device for communication over the WAN. Optionally, the provider-side device can be any type of computing device, such as a computer, PDA, etc.

By receiving data from the patient-side device, a provider is able to monitor the patient/client's physiology for research, keeping track of documentation, performing analysis, managing and maintaining records, diagnosing the patient/client, providing treatment in real-time to the patient/client, etc. Additionally, the patient/client may be remotely "examined" by an expert or other medical personnel when one is not physically available or accessible. Such situations may occur, for example, when a patient/client or provider is in or on an airplane or ship, or when the patient/client or provider is located in a different part of the world. The present invention also allows for daily or periodic monitoring of patients without the need for the patient/client to travel to the provider's location. This is ideal for nursing homes and home care patients.

The devices on the patient/client and/or provider sides may allow for various forms of bidirectional communication including, but not limited to instant messaging, an integrated e-mail system, real-time video, and real time audio. Preferably, the communications are provided via a browser-based interface. Further, the provider may remotely control the client-side device. For example, when the patient is sleeping in his/her home with EKG and blood pressure devices connected, the provider can start these devices remotely to read the data periodically or whenever needed.

Alerts may be sent upon occurrence of an event recognized in the data. For example, based on real-time streaming of vital patient/client information, the present system may be tailored to forward proper responses to the patient/client. One of the communication modes described above may be set up to allow for rapid communications to the patient/client or provider in an emergency situation.

Whether or not the provider is not currently accessing real-time streamed information, the data may be stored in a secured storage device for later access, replay, and/or analysis. The storage device may also be used to store all patient data or information. Thus, the exemplary embodiment may allow for simultaneous storage, retrieval, print, analysis, and play back from anywhere in the world with access to the storage device.

Preferably, the present invention is built on a modular architecture in which the patient-side device and/or the computing device coupled to the patient-side device can send a request to the engine with an identifier of the patient-side device, and the engine will send the appropriate plug-in which allows the computing device to communicate with the patient-side device. Thus, the present invention may support both plug-and-play web device drivers and customized graphical user interfaces (GUIs) for the various devices. Existing devices (which are not web-enabled) may be easily web-enabled by installation of the appropriate plug-and-play driver and GUI. Thus, virtually any device may be easily incorporated into the system.

A fee may be charged for transmitting the data, storing the data, etc.

A method for network-based communication of medical-related data from a patient-side device according to one embodiment includes communicating with a computing device from a central site remote from the computing device using a wide area network, the computing device being coupled to a patient-side device, the patient-side device being for collecting physiological data from a patient; communicating with a second device from a central site remote from the second device using the wide area network, the second device being remote from the patient-side device; managing transmission of data from the computing device to the second device; and allowing a user to remotely control at least some function of the computing device or patient-side device via the second device, the function relating to collection of the physiological data 12.

A method for network-based monitoring of physiological data according to another embodiment includes uploading software from a central site to at least one patient-side device, the software enabling collection of the physiological data from at least one of directly from a patient, the at least one patient-side device, and a second device coupled to the at least one patient-side device; collecting physiological data from the patient utilizing the at least one patient-side device; and managing a transmission of the physiological data from the at least one patient-side device to a provider-side device, wherein the software is only active when the at least one patient-side device is connected to the central site, wherein the central site includes at least one server, at least one data storage device, and at least one wide area network interface.

The present invention may be implemented on a program or code that can be stored in a computer-readable (or electronically-readable) medium.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

FIG. 8 depicts an illustrative screen from which the patient and/or provider can access stored sessions.

FIG. 9 illustrates an exemplary screen from which a sponsor can select patients of a particular provider and view information about the patients.

FIG. 14 depicts a Sponsor submodule of the Registration module.

FIG. 15 illustrates a Service Provider submodule of the Registration module.

BEST MODE FOR CARRYING OUT THE INVENTION

The following description is the best embodiment presently contemplated for carrying out the present invention. This description is made for the purpose of illustrating the general principles of the present invention and is not meant to limit the inventive concepts claimed herein.

System Architecture

Figure 1A:
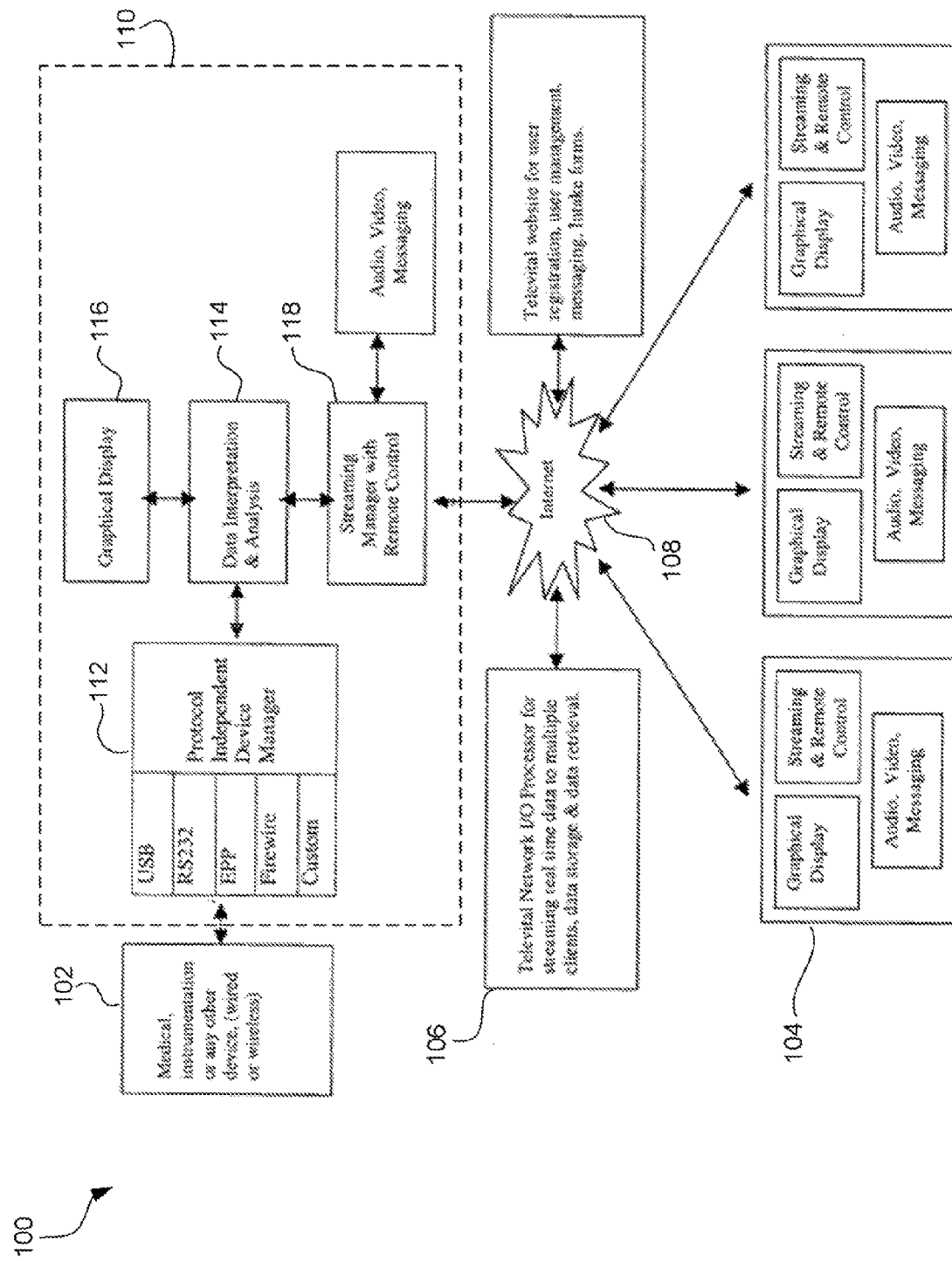
FIG. 1A is a diagram of an exemplary system architecture for network-based monitoring of data from a patient-side physiological collecting data according to one illustrative embodiment.

FIG. 1A is a diagram of an exemplary system architecture 100 for network-based monitoring of data from a patient-side physiological collecting device according to one illustrative embodiment. As shown, the system includes one or more patient-side devices 102 for collecting data from a patient/client, one or more provider-side devices 104, and an engine implemented on a central server 106. The devices and engine are connected to a wide area network (WAN) 108 such as the Internet, intranet, or extranet. The system allows for the real-time streaming of raw, interpreted, and/or processed physiological data as well as textual/audio/video data from a patient to a health care provider. However, other embodiments may contemplate non-medical/non-biofeedback devices and non-human monitoring.

The integration of biomedical and/or biofeedback devices along with the connection between service providers and patients allows for many applications, including but not limited to: telemedicine, remote sleep studies, physical evaluations, remote monitoring, event recordings, holter monitoring, home health care, disease management applications, biofeedback, pharmaceutical research, wireless monitoring, anesthesiology-related monitoring, and stress, health and wellness education.

The embodiments presented herein contemplate connection of multiple patient-side devices, provider-side devices, and engines/central servers. Because a plurality of devices and engines may be in operation, the system may be capable of networking the numerous devices and/or engines into individual, group, clinic, hospital, or other electronic record systems. For simplicity, the discussion will proceed with description of a system having a single patient-side device, provider-side device, and engine/central server; it being understood that one skilled in the art would be able to use the system with multiple devices connected without undue experimentation.

Use of the term "patient" is not intended to limit application of the embodiments presented here to medical patients. Rather, patients can include anyone whose biophysical data is being read, healthy or not. Note also that a "provider" as used herein can be a medical provider such as a doctor, nurse, etc., but also includes any recipient of the data, whether affiliated with health care or not. For example, such a recipient could be researcher gathering statistics, a device manufacturer monitoring operation of the device or debugging the device, etc.

The patient-side device is located with a patient and can be any device that gathers physiological data from the patient. Illustrative patient-side devices include, but are not limited to, telemetry EKG, EMG and EEG monitors; continuous blood pressure and blood glucose watches; cellular transmission holter monitors; wireless plethysmograph rings; automated IBS and depression multimedia protocols; T-shirts wired with sensors that monitor and record physical and emotional indicators derived from heart activity, breathing patterns and blood pressure, bracelets, earrings and necklaces that monitor physiological activity; implanted devices that capture and transmits a person's vital body-function data, such as body temperature or pulse, to an internet-integrated ground station while providing global positioning information.

Figure 1B:
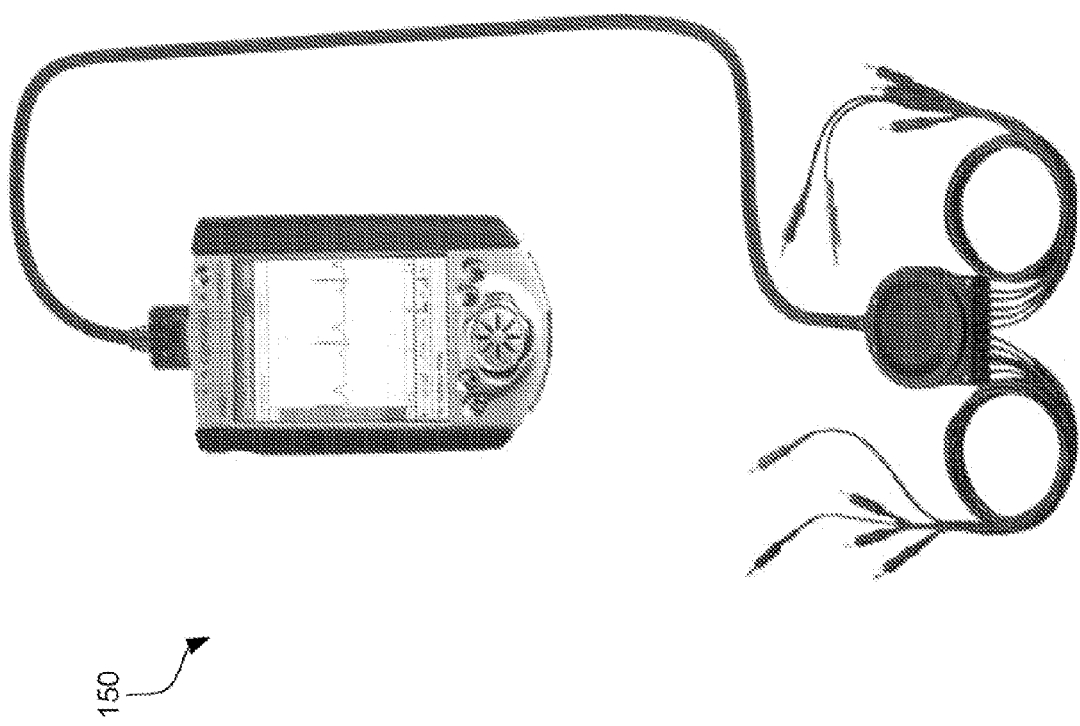
FIG. 1B illustrates browser-based real-time 3 lead and spirometry transmitting, viewing and receiving on a wireless Internet connection using a pocket PC.

The patient-side device may then be connected via a computing device 110, such as a computer, handheld devices such as personal digital assistants (PDAs) and pocket PCs such as IPAQ with Windows CE operating System and Palm devices based on Palm OS), wireless telephone, or any other computing device, to the WAN. Optionally, the patient-side device may have a built-in computing device for communication over the WAN. A protocol independent device manager 112 running on the computing device establishes a two-way communication with a vast array of client-side devices, including but not limited to medical and/or biofeedback devices, holter monitors, telemetry units, data acquisition units, etc. Each patient-side device can be wired or wireless, and communicates through a serial (RS232, USB, IEEE 1394, etc.), parallel, fire-wire, wireless, or customized interface/protocol. Similarly, the provider-side device can be any type of computing device, such as a computer, PDA, wireless telephone, etc. In one embodiment, the provider's computing device (such as a PDA or telephone) has a wireless connection to the WAN so that, even though the doctor is not at a hospital or in his office, he may still be consulted remotely without the need to rush to the hospital. FIG. 1B illustrates browser-based real-time 3 lead and spirometry transmitting, viewing the receiving on a wireless Internet connection using a pocket PC 150.

The connection to the WAN (such as the Internet) can include dialup (56K), satellite phones, Iridium phones, ISDN, T1, DSL, cable modem, wireless connection, etc.

Preferably, the present invention is built on a modular architecture in which the patient-side device and/or the computing device coupled to the patient-side device can send a request to the engine with an identifier of the patient-side device, and the engine will send the appropriate plug-in which allows the computing device to communicate with the patient-side device. Thus, the present invention may support both plug-and-play web device drivers and customized graphical user interfaces (GUIs) for the various devices. Existing devices (which are not web-enabled) may be easily web-enabled by installation of the appropriate plug-and-play driver and GUI. Thus, virtually any device may be easily incorporated into the system. These teachings can also apply to the provider-side device.

The data interpretation and analysis module 114 is used to interpret the data stream from the client-side device, perform mathematical analysis on the data using FFT, DFT, etc., and generate statistics. The data may be displayed graphically on the display module 116.

The data may also be simultaneously streamed to multiple remote providers over the WAN so that the remote providers can view the data in real time. The streaming manager 118 is responsible for managing transmission of the data to the remote providers, including, optionally, encrypting and compressing the data.

The real time streaming of ECG, EEG, EMG, blood-gas readings, respiration, and other medical wave-forms can be supported by threshold and alarm controls, real-time and/or post-session analysis, email, teleconference medias, and storage, retrieval and replay of raw or interpreted data from any WAN connection, including a dialup Internet connection.

By receiving data from the patient-side device, a provider is able to monitor the patient's physiology for research, keeping track of documentation, performing analysis, managing and maintaining records, diagnosing the patient, providing treatment in real-time to the patient, etc. Additionally, the patient may be "examined" by an expert or other medical personnel when one is not physically available or accessible. Such situations may occur, for example, when a patient or provider is in or on an airplane or ship, or when the patient or provider is located in a different part of the world. The present invention also allows for daily or periodic monitoring of patients without the need for the patient to travel to the provider's location. This is ideal for nursing homes and home care patients.

Depending on available bandwidth, the system may allow for the real-time streaming of raw, interpreted, and processed physiological data as well as textual/audio/video data from a patient to a health care provider. For example, the devices on the patient and/or provider sides may allow for various forms of communication including, but not limited to instant messaging, an integrated e-mail system, real-time video, and real time audio. The audio and/or video can be synchronized with the biomedical signals to help correlate behavior with physiological activity. Preferably, the communications are provided via a browser-based interface.

Using optional remote control features built in to the system, remote providers can control the software on the patient's end. Thus, patients do not need to know how to operate the software.

Preferably, the engine manages transmission of the data from the patient-side device to the provider-side device. This means that the engine may configure the devices to transfer the data directly from one device to the other; may receive the data from the patient-side device and transmit the raw or processed data to the provider-side device; may store the data for later transmission to the provider-side device, etc.

The network I/O processor running the engine preferably forms the core of the real time streaming portion of the engine. The I/O processor is responsible for streaming device data, audio, video, messages, and remote control information between multiple clients and hosts. The processor may also handle data storage and retrieval of the streamed data.

Whether or not the provider is currently accessing real-time streamed information, the data may be stored in a secured storage device at the central server for later access, replay, and/or analysis. The storage device may also be used to store all patient data or information, and integrate the data, whether as raw data, trended data, or summary data, into any electronic medical records system, for example. Thus, the exemplary embodiment may allow for simultaneous storage, retrieval, print, analysis, and play back from anywhere in the world with access to the storage device. This beneficially allows a provider to seek expert consultation for clinically difficult cases, by sharing the patient history and medical test results online. Further, storage of the data allows for the creation of statistical databases, including development of a database of biomedical test results, for example. For example the results of routine medical tests may be stored from the biomedical device directly into the patient's electronic medical record. Further, personal health information can be stored in smart-cards that can be carried by a patient, and which may also carry other personal information such as credit card and back account data.

The system may also track trends during the recording, and using artificial intelligence, predict future behaviors and physiological responses based on the habits of the particular client hooked up.

A remote client module (not shown) allows remote hosts to view the data being streamed in real time. The remote client module can also control the software being run on the patient's and/or provider's end. Multiple remote client modules can run concurrently, allowing multiple remote providers to view data from one device.

Preferably, the entire system runs in the context of an Internet browser. Integration of the client-side device driver is performed in two steps. First, the appropriate device driver is incorporated into the system, preferably via a web page. A customized or standard GUI is incorporated or developed based on user and/or device manager specifications. Thus, a user does not have to install any software, and updates to the software are done by simply running the latest software from a website.

The present invention may be implemented on a program or code that can be stored in a computer-readable (or electronically-readable) medium. The system may be implemented using Apache web server, MySql on Linux, Oracle on Linux, Java servlets, Applets, HTML, JavaScript, Java, C#, Microsoft's .NET etc. Note also that the server may be implemented on the Internet, intranet, or an extranet.

Alerts may be sent upon occurrence of an event recognized in the data. For example, based on real-time streaming of vital patient information, the present system may be tailored to forward proper responses to the patient. One of the communication modes described above may be set up to allow for rapid communications to the patient or provider in an emergency situation.

Figure 2:
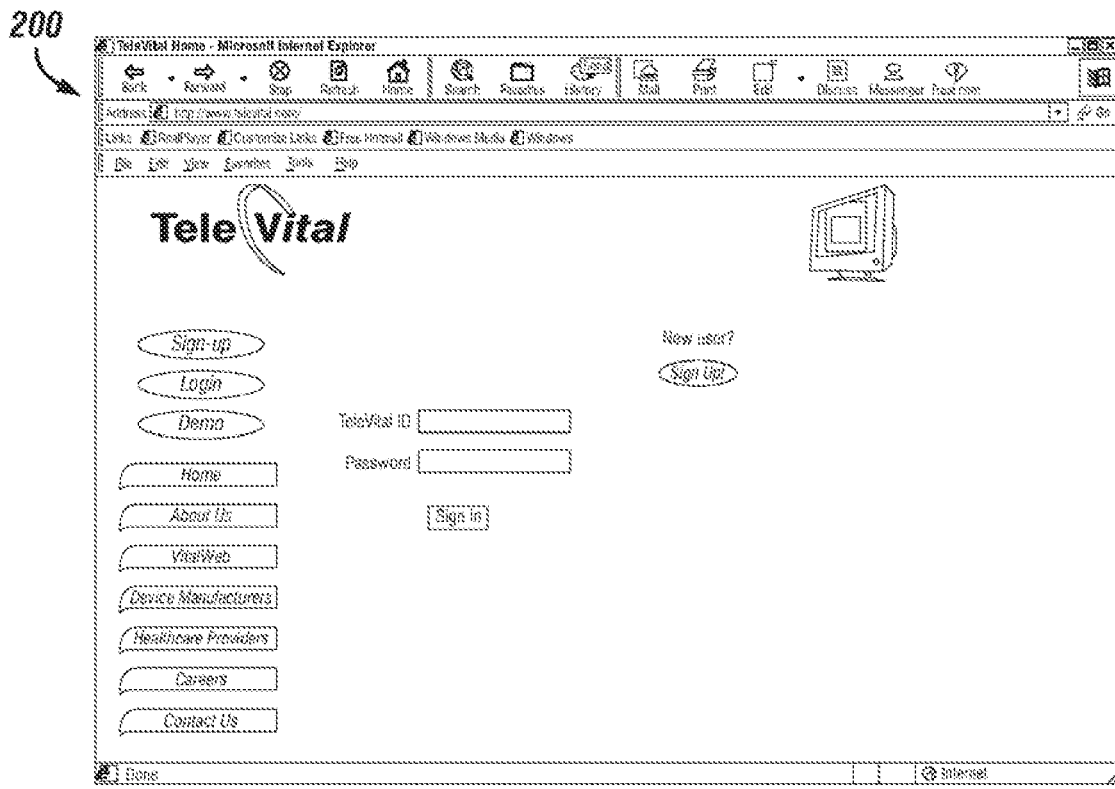
FIG. 2 depicts an illustrative patient login screen.
Figure 3:
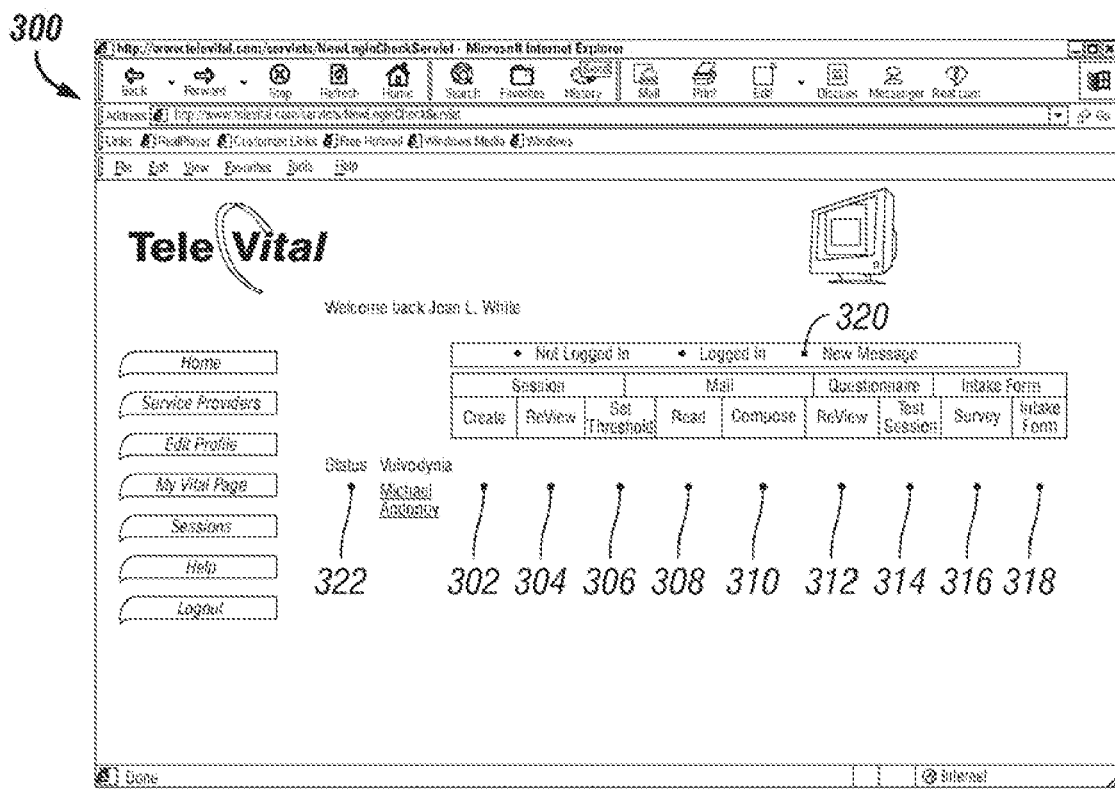
FIG. 3 shows an illustrative screen displayed upon patient login.

In an example of use during a remote session, a patient is connected to a patient-side biophysical monitoring device, such as by adherence of the appropriate sensors to the patient's body. The sensors are coupled to a medical and/or biofeedback patient-side device that is in wireless or wired communication with a computing device. Such patient-side device may include, but is not limited to, EKG, EMG, EEG, and body temperature monitoring devices. FIG. 2 depicts an illustrative login screen 200, from which the patient then logs on to a website with a secure logon ID and password, thereby creating a session. The screen 300 shown in FIG. 3 is displayed. On this screen, the user can create a session by selecting button 302, review a prior session by selecting button 304, set a threshold for an alert by selecting button 306, read mail by selecting button 308, compose mail by selecting button 310, review a previously answered questionnaire by selecting button 312, fill out new questionnaires/surveys by selecting buttons 314 or 316 respectively, and fill out or amend an intake from by selecting button 318. A button 320 can be colored or lighted when the patient has new messages. The patient's remote healthcare provider is listed and the patient is notified if the provider is online, such as via a flashing "live" button 322.

Figure 4:
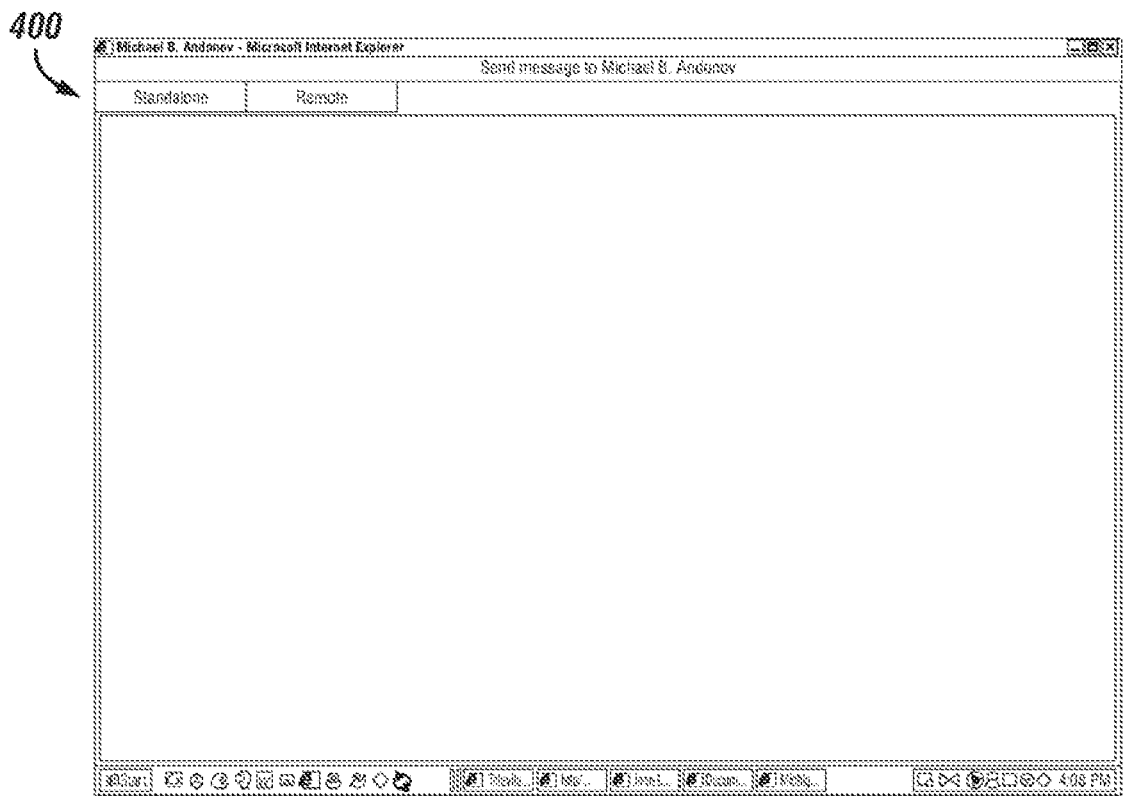
FIG. 4 illustrates a messaging screen.

FIG. 4 illustrates a messaging screen 400 displayed upon selection of the compose mail button shown in FIG. 3. Note that the patient can select a standalone or remote mode.

Figure 5:
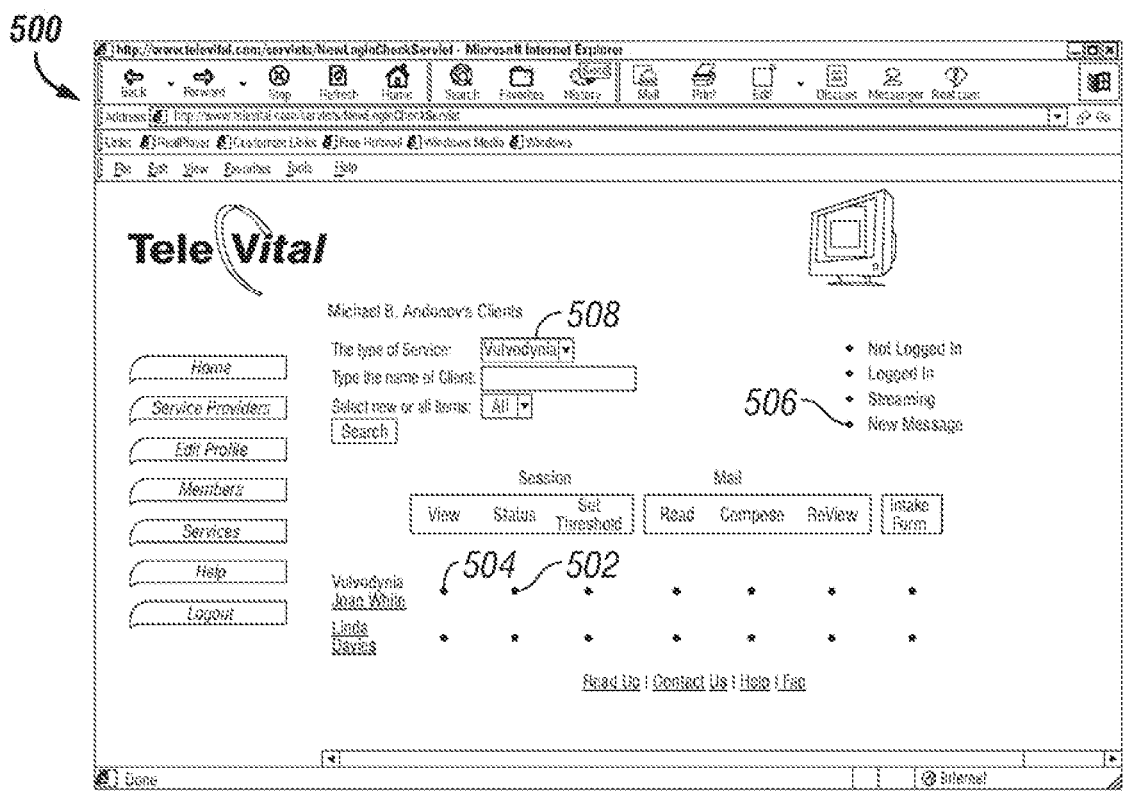
FIG. 5 depicts an illustrative screen displayed to a provider.

The provider's patients are listed on a screen 500 such as the screen shown in FIG. 5. A healthcare provider is notified that a session is in progress, such as via a flashing "live" button 502. The provider can view streaming and/or saved data relating to the patient by selecting button 504. The screen can also provide access to messaging functions, as well as receipt of a new email message, page, etc. Also, the provider can view the intake form of the patient by selecting button 506. Patients may be sorted by type of service from menu 508.

Figure 6:
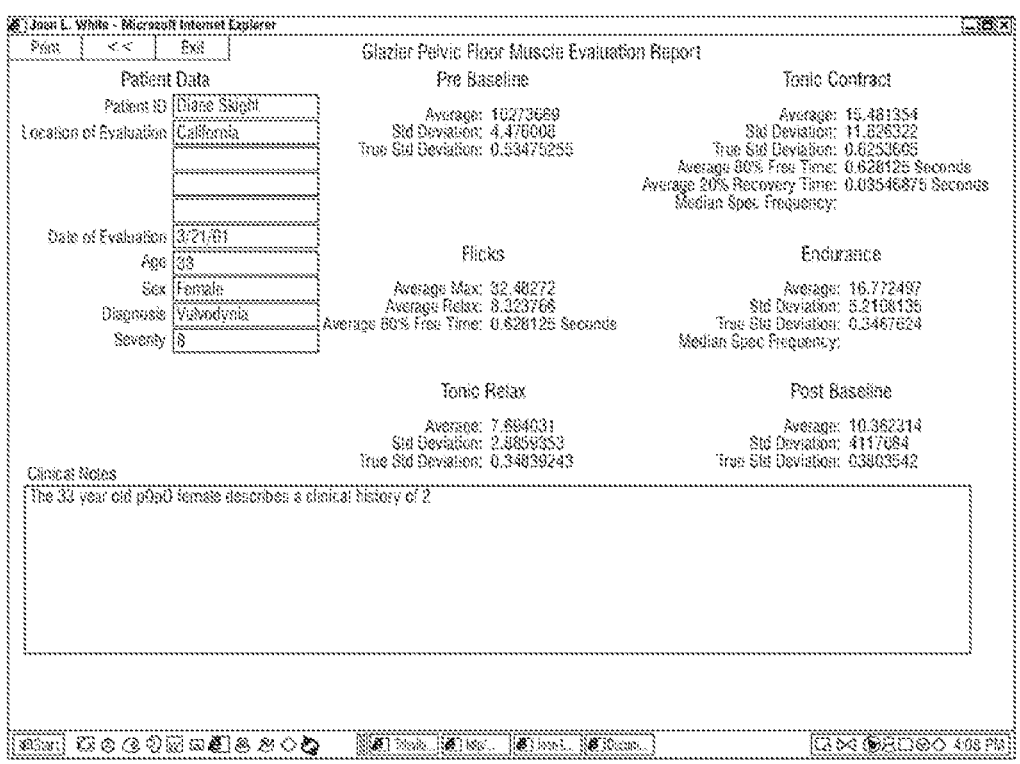
FIG. 6 shows an exemplary statistical summary screen.
Figure 7:
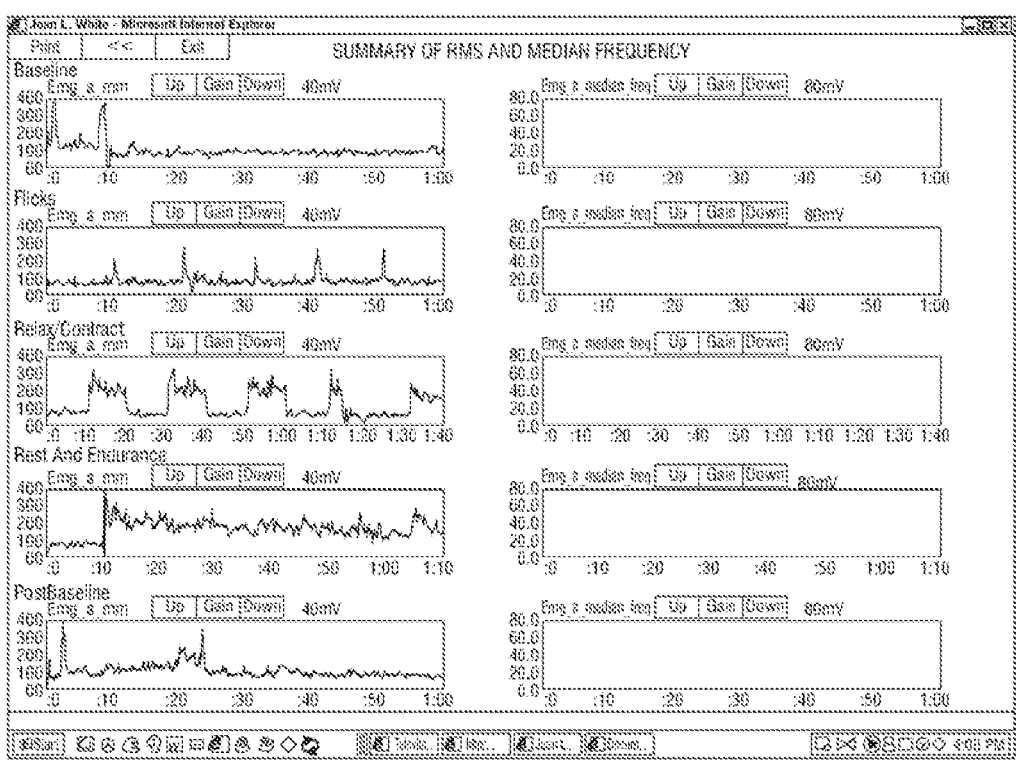
FIG. 7 shows an exemplary screen of a graphical report.

By joining the session, the healthcare provider can immediately view their patient's real-physiological data by selecting button 504. The healthcare provider can remotely adjust the gain for optimal display, and both parties have the option to communicate with the built-in instant messaging feature, or an external or integrated audio or visual device. At the end of a session, the healthcare provider can view a statistical summary report 600, shown in FIG. 6 and that includes a field for adding clinical notes. FIG. 7 shows a screen 700 of a graphical report that can also be displayed. Either can be displayed on both ends, and can even be remotely printed for the client. All sessions may be dated and stored for retrieval by either party at a later date.

Figures 8, 9:
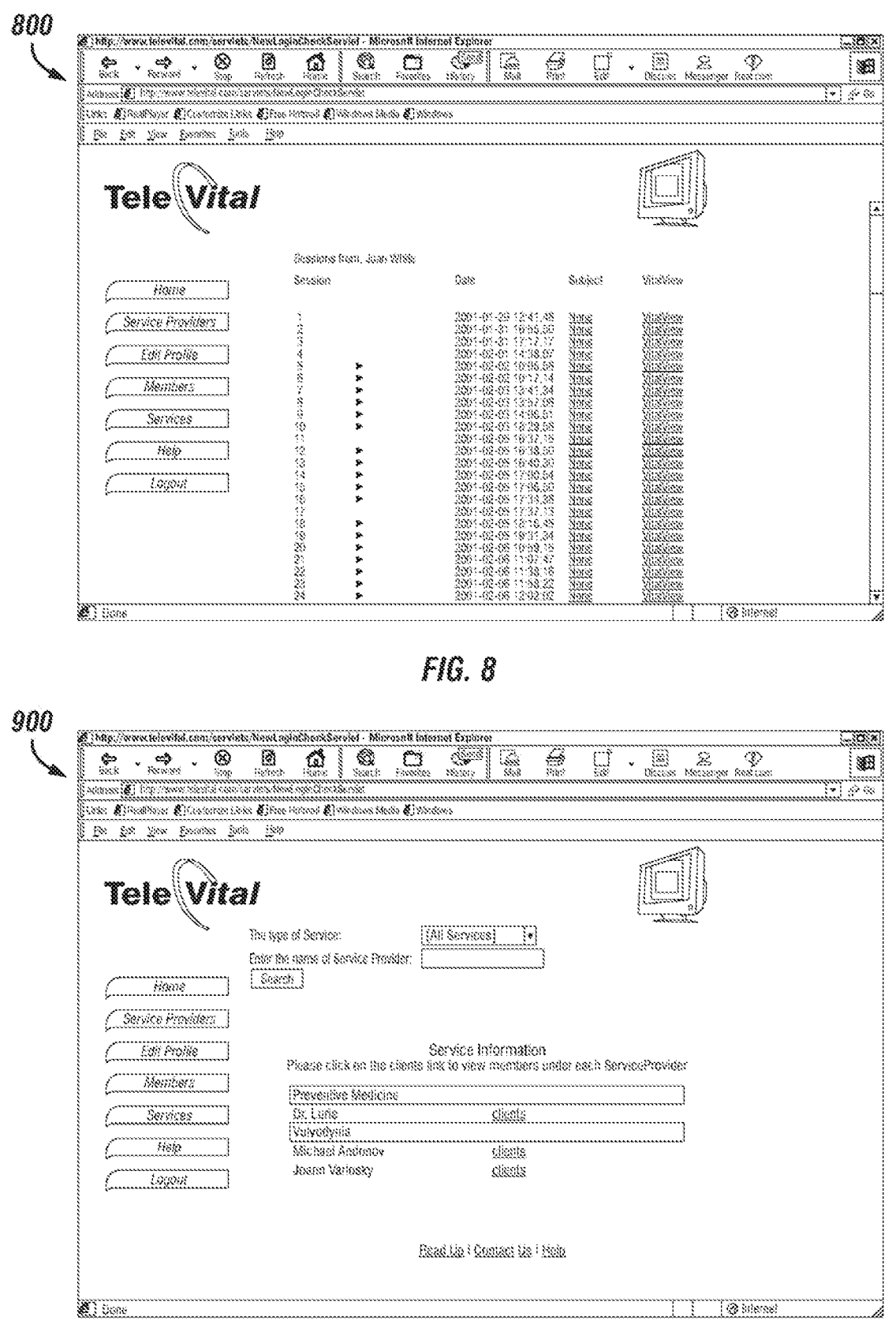

FIG. 8 depicts a screen 800 from which the patient and/or provider can access stored sessions. FIG. 9 depicts a screen 900 from which a sponsor can select patients of a particular provider and view information about the patients. Providers/patients can be sorted by type of service. Upon selecting a provider, a screen similar to that shown in FIG. 5 may be displayed, and similar functionality provided, if the sponsor has appropriate privileges.

Figure 10:
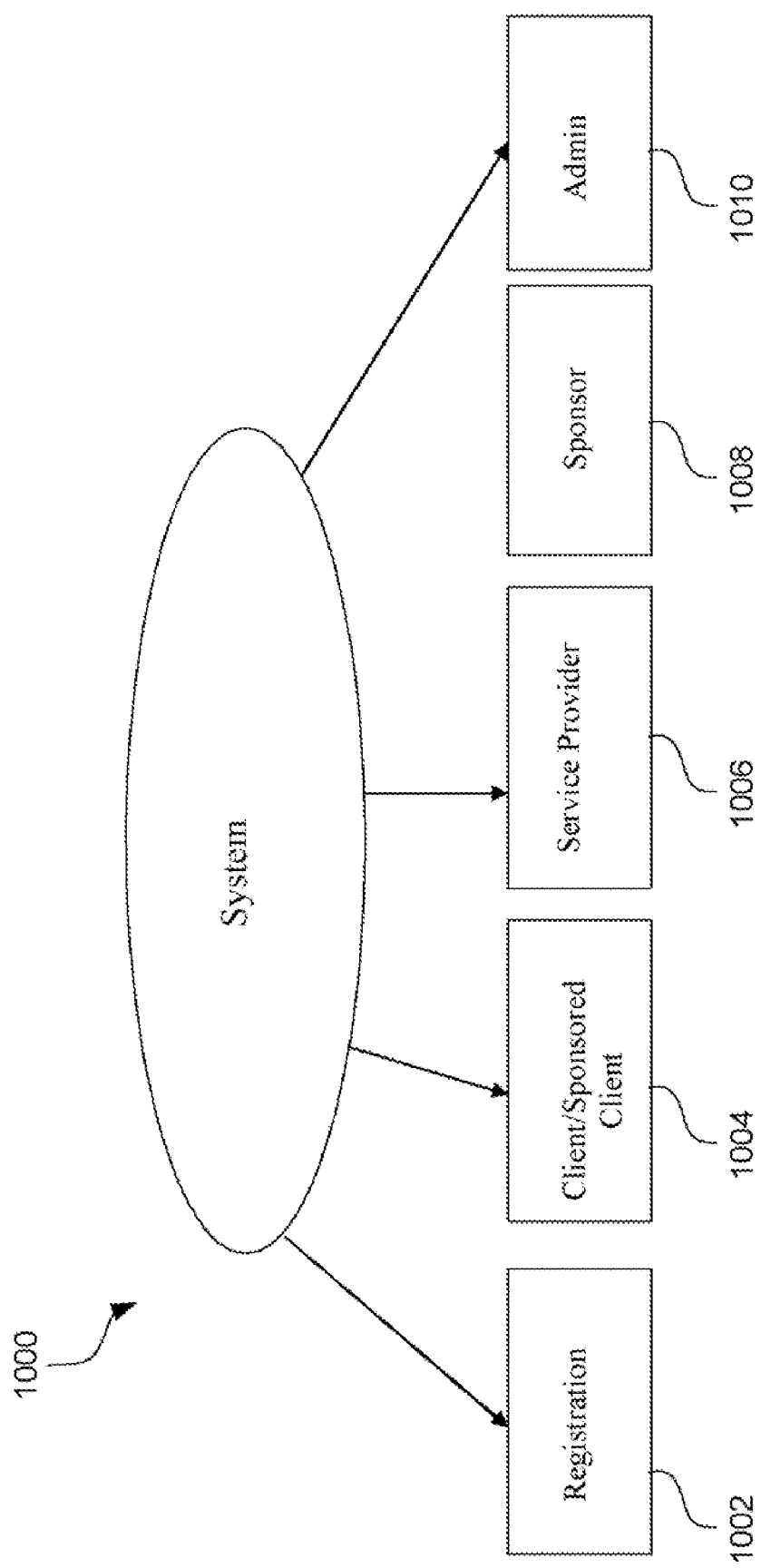
FIG. 10 depicts a modular view of a system according to an exemplary embodiment.

FIG. 10 depicts a modular view of the system 1000 according to an exemplary embodiment. As shown, the five major modules include Registration 1002, Client/Sponsored Client 1004, Service Provider 1006, Sponsor 1008 and Admin 1010. Following is explanation for all the modules.

Config.java is a general class used by all the Java servlets, and may include a method similar to:
RemoveSpace( )
RemoveBlanks( )
ConverMonth( )
ConvertClientType( )
InsertEscape( )
HandleDouble( )
Replace( )
GetURI( )
GetDriver( )
GetUser( )
GetPassword( )
GetAdminName( )
GetAdminPassword( )

Database specific parameters like UserName, Password etc. can be changed here. AdminName and AdminPassword can also be fixed here.

Figure 11:
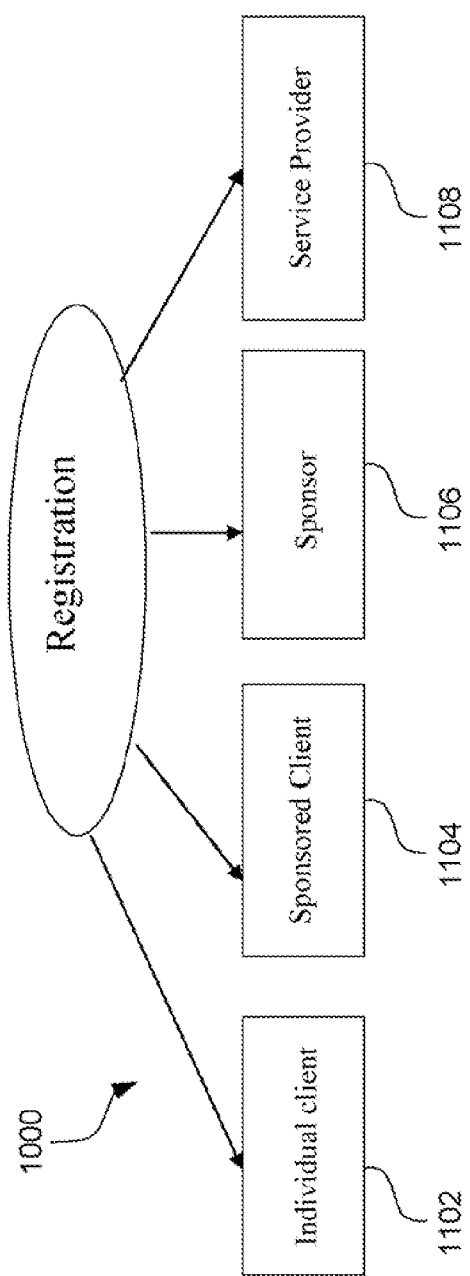
FIG. 11 illustrates a Registration module of the system shown in FIG. 10.
Figure 12:
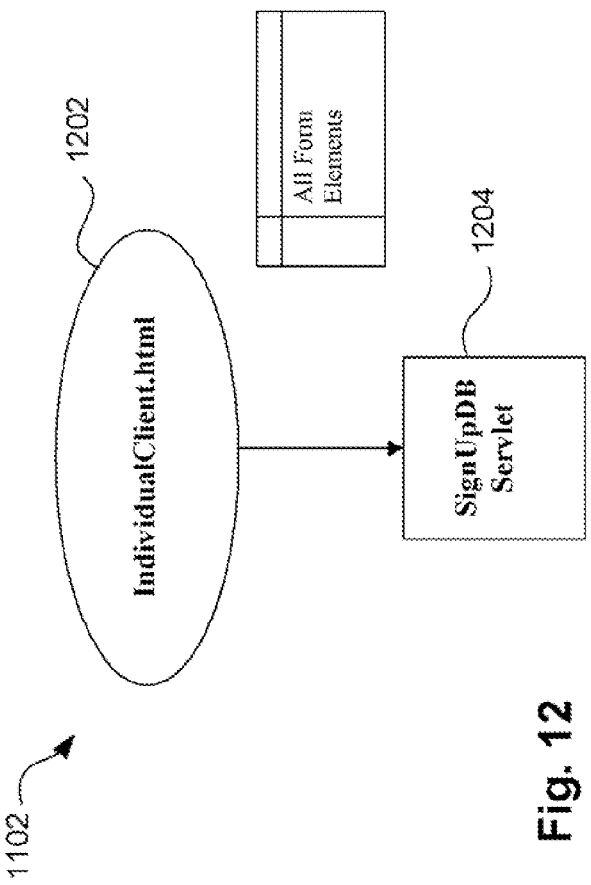
FIG. 12 depicts a Client submodule of the Registration module.

FIG. 11 illustrates the Registration module. The Individual Client submodule 1102, shown in FIG. 12, includes a form 1202 to enter a user profile and a java servlet 1204 to write information to a profile database.

Figure 13:
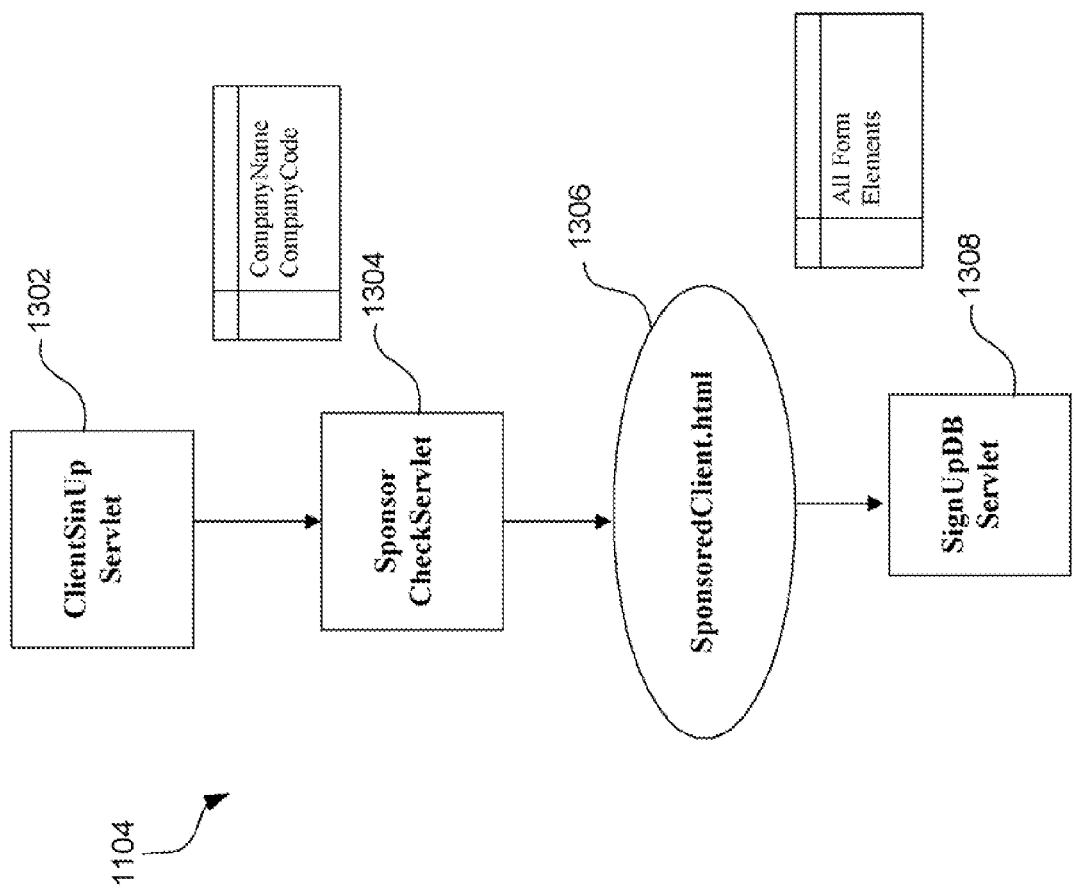
FIG. 13 shows a Sponsored Client submodule of the Registration module.

As shown in FIG. 13, the Sponsored Client submodule 1104 includes a servlet 1032 that displays existing Sponsors and a servlet 1304 that checks authentication. For example, a company name and authentication code can be input from an HTML form 1305. If the authentication is successful, a form 1306 is displayed to enter his/her profile, and a servlet 1308 writes the information to the profile database.

The Sponsor submodule 1106, shown in FIG. 14, includes a form 1402 to enter sponsor profile, and a servlet 1404 that writes information to the Profile database. Random number generation is used to allocate an authentication code and Java mail API is used to send the authentication code.

As depicted in FIG. 15, the Service Provider submodule 1108 includes a form to enter the Service Provider's personal profile and a servlet 1502 which takes his professional information. This servlet gets all input from the form and converts it to a SQL statement and stores it in a session prior to being sent to a servlet 1504 which stores personal information in the session, and a servlet 1506 that writes personal information into the profile database and professional information into a therapy database.

Figure 16:
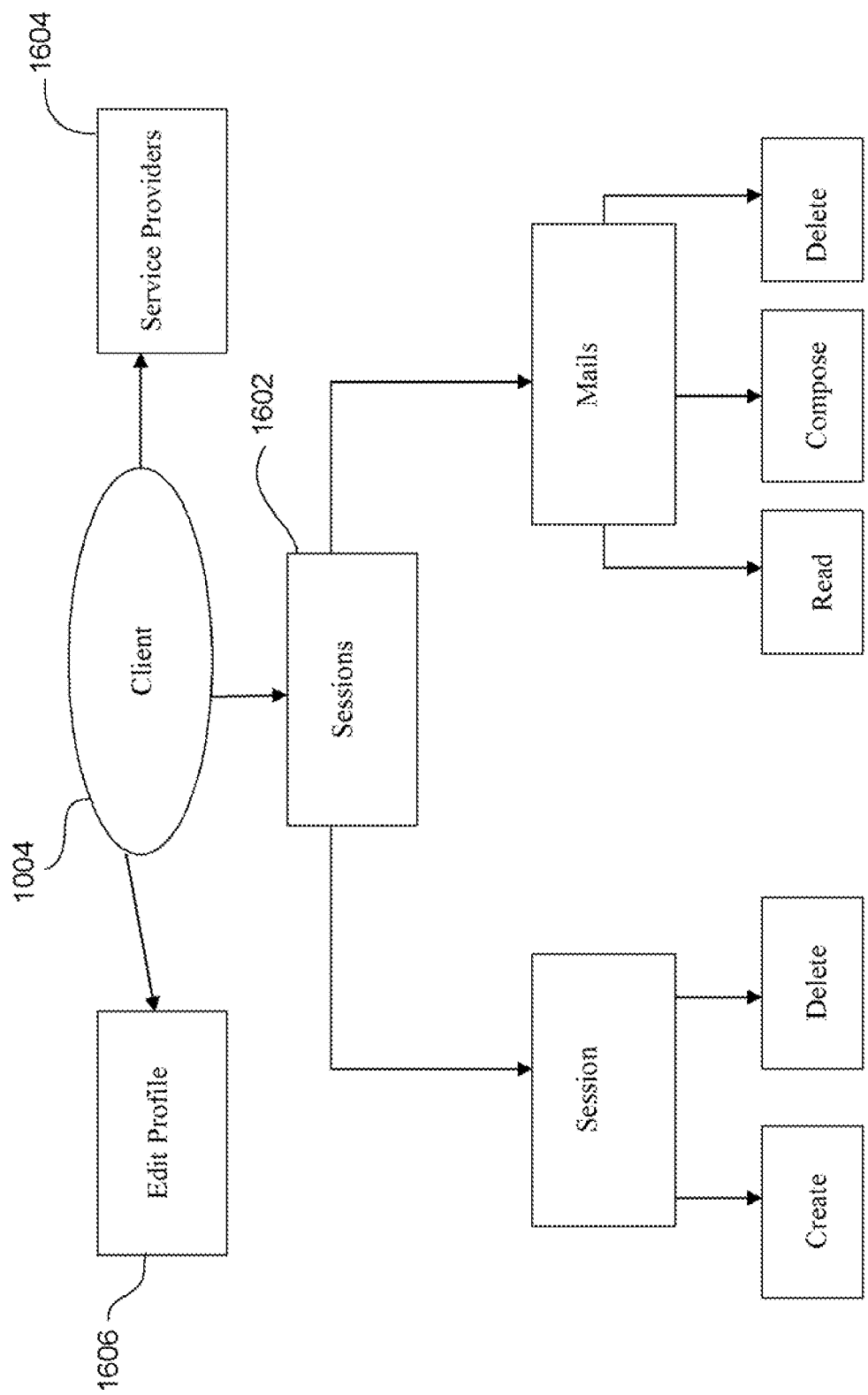
FIG. 16 depicts the Client/Sponsored Client module of the system shown in FIG. 10.

FIG. 16 depicts the Client/Sponsored Client module that includes a Sessions submodule 1602, a Service Providers submodule 1604, and an Edit Profile submodule 1606.

Figure 17:
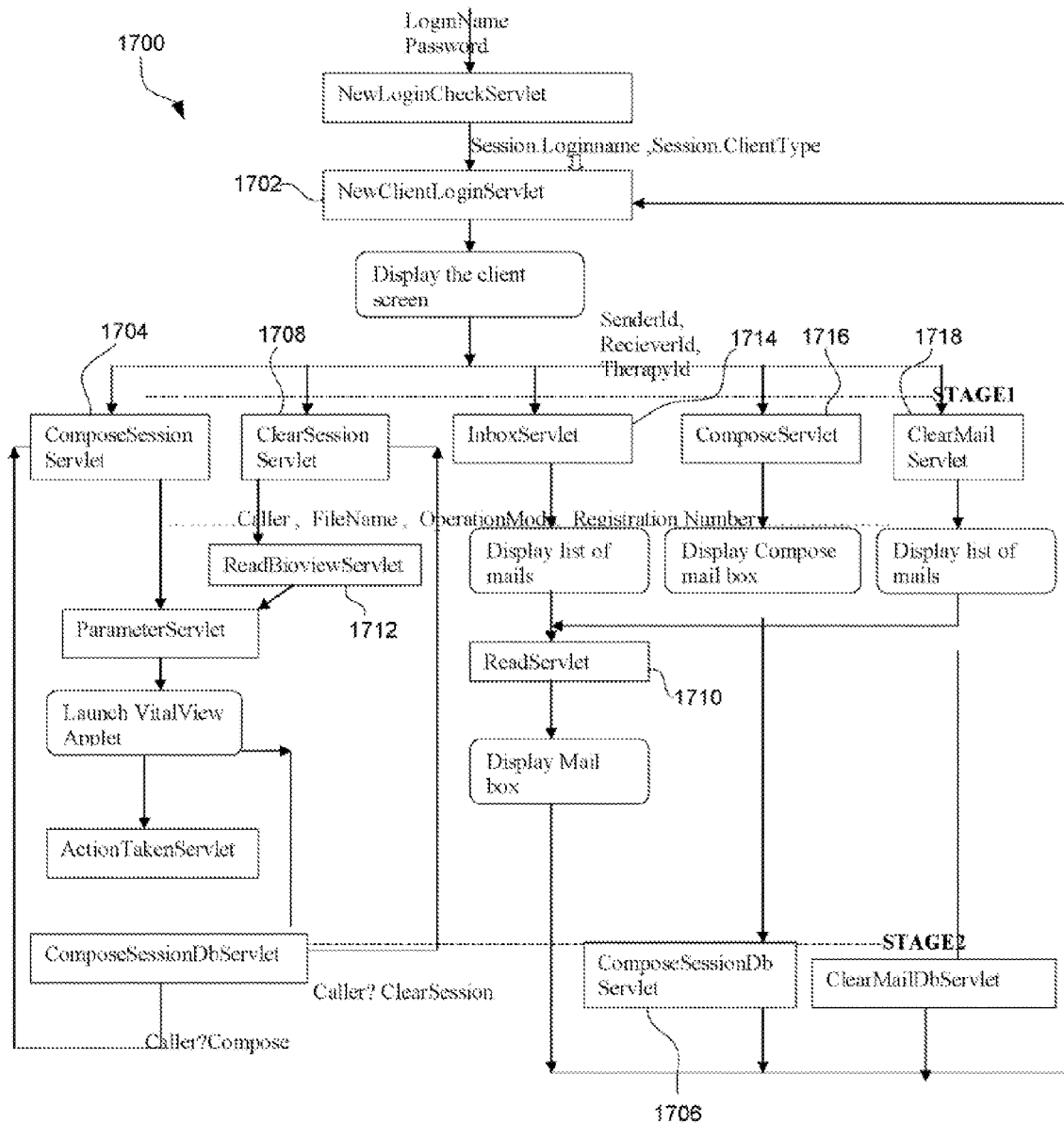
FIG. 17 is a data flow and control flow diagram for a Sessions submodule of the Client module.

FIG. 17 is a data flow and control flow diagram 1700 for the Sessions submodule of the Client module. The Sessions submodule includes a servlet 1702 that displays a Client's/Sponsored Client's active area on a client screen. Red colored gifts indicate that there is new message/session. Every client has a unique loginid. The servlet requires these inputs for the identification of the client.

To create a session, a servlet 1704 launches an applet that collects bio-medical data from the client and streams it to Service Provider. Another servlet enables the client to attach a message to session. Yet another servlet 1706 writes to the session database. Servlet 1708 displays the sessions sent by the client with option to delete. Servlet 1710 reads the messages sent with the session. Servlet 1712 launches an applet which displays bio-medical data stored in server. A servlet deletes records from the session database.

To enable mail functions, a servlet 1714 displays mails sent by the Service Provider. Servlet 1710 reads mails sent by Service Provider and updates the read flag in the mail database. Servlet 1716 enables clients to compose mails. Another servlet writes to mail a database. Servlet 1718 displays mails sent by the Client with an option to delete. Another servlet may be provided to delete mails sent by the Client from mail database.

The input for the Stage1 servlets include:
SenderId—the id of the sender of this mail/session
ReceiverId—the id of the receiver of this session
TherapyId—the therapy from/to this mail/session is being sent The output for the Stage1 servlets include:
Caller—The calling servlet name
FileName—the filename of the session/mail sent/received
OperationMod—the action to be performed on this session
Registration Number—this uniqueid is required in order to identify the sender & receiver of the packet The Stage2 servlets are the DB servlets whose function is to update the changes in the database & return the control to the caller servlet. The input for the Stage2 servlets include are the same as shown, and further include callerID.

The input for servlets that read mail can include:
Caller—The calling servlet name
FileName—the filename of the session/mail sent/received
OperationMod—the action to be performed on this session
Registration Number—this unique ID is required in order to identify the sender & receiver of the packet A servlet may be provided that allows client to modify his profile information. Input for this servlet can include:
  Name—Login name of the user who profile has to be modified
  ClientType—The type of client
  ServletName—The name of the calling servlet
The output for this servlet may include all of the form inputs plus the Input of this servlet.

A further servlet updates modifications of the profile database. Inputs to this servlet include all the parameter output by the servlet that allows modification of profile information. This servlet further updates the database for changes and returns control to the respective servlet based on the caller.

Figure 18:
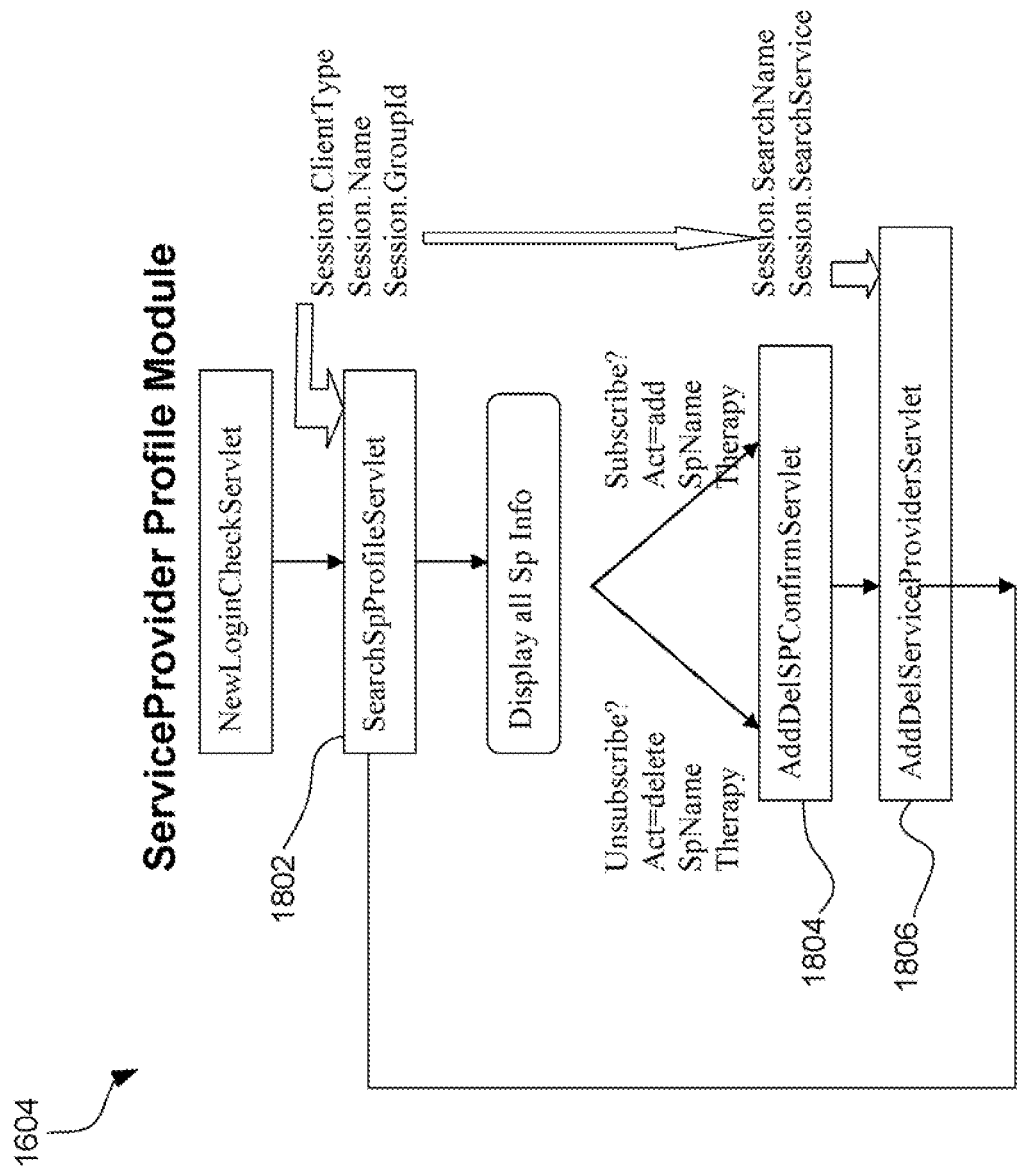
FIG. 18 depicts a Service Providers profile submodule of the Client module.

FIG. 18 depicts the Service Providers profile submodule 1604 of the Client module. The Service Provides submodule includes a servlet 1802 that displays all Service Providers for an individual client with an option to subscribe/unsubscribe. For sponsored clients it displays all service providers with an option to subscribe/unsubscribe only sponsor selected service providers. This also includes a search facility. Another servlet 1804 asks for confirmation before subscribe or unsubscribe a service provider. A further servlet 1806 adds or deletes a record from the registration database.

Figure 19:
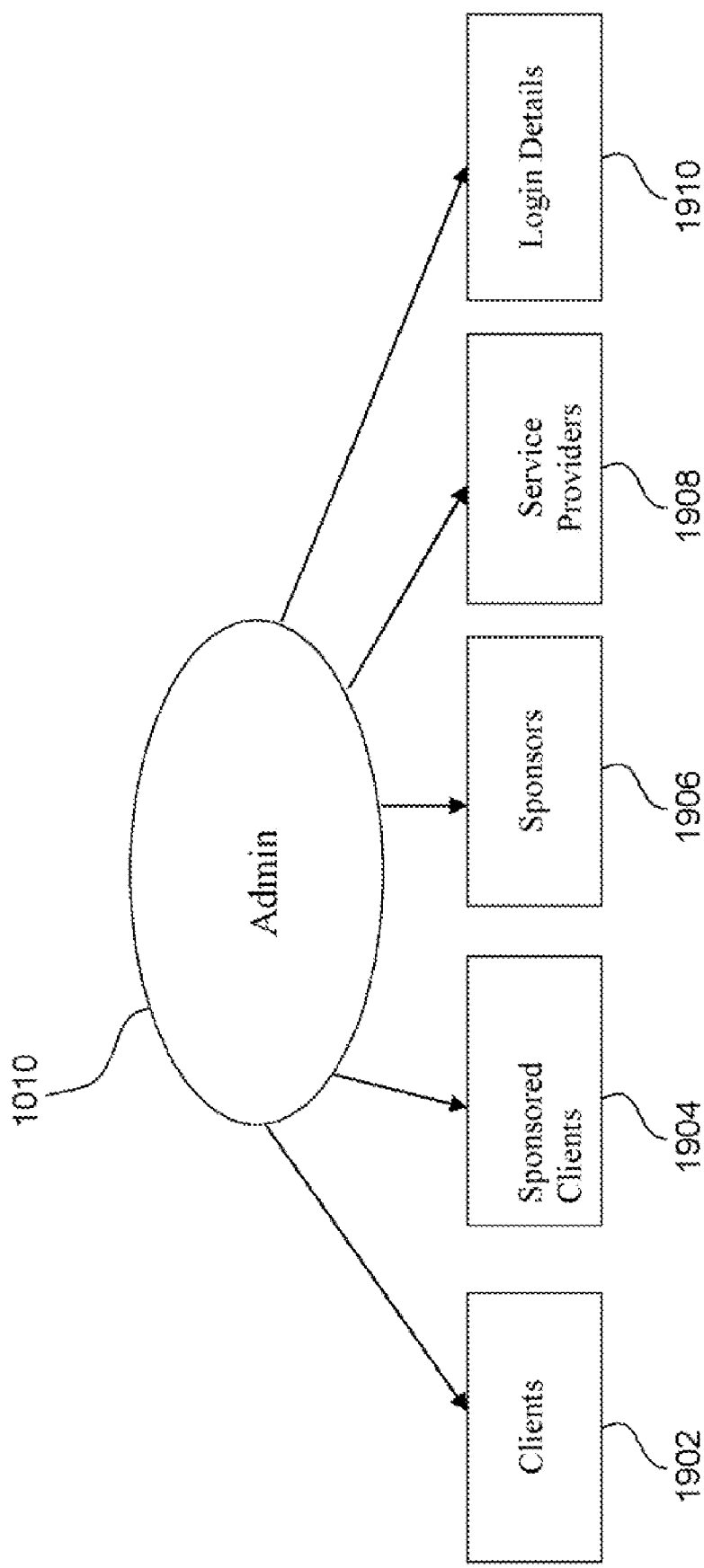
FIG. 19 shows an Admin module of the system shown in FIG. 10.

FIG. 19 shows the Admin module 1010. The Clients submodule 1902 includes servlets that display disabled clients, display enabled clients, enable or disable the client, and modify the profile of the client. The SponsoredClients submodule 1904 includes servlets that display disabled sponsored clients, display enabled sponsored clients, enable or disable the client, and modify the profile of the sponsored client. The Sponsors submodule 1906 includes servlets that display disabled sponsors, display enabled sponsors, enable or disable the sponsors, and modify the profile of sponsors. The Service Providers submodule 1908 includes servlets that display disabled service providers, display enabled service providers, enable or disable the service providers, and modify the profile of service providers. The Login Details submodule 1910 includes servlets that provide login details of all and includes a search facility.

Figure 20:
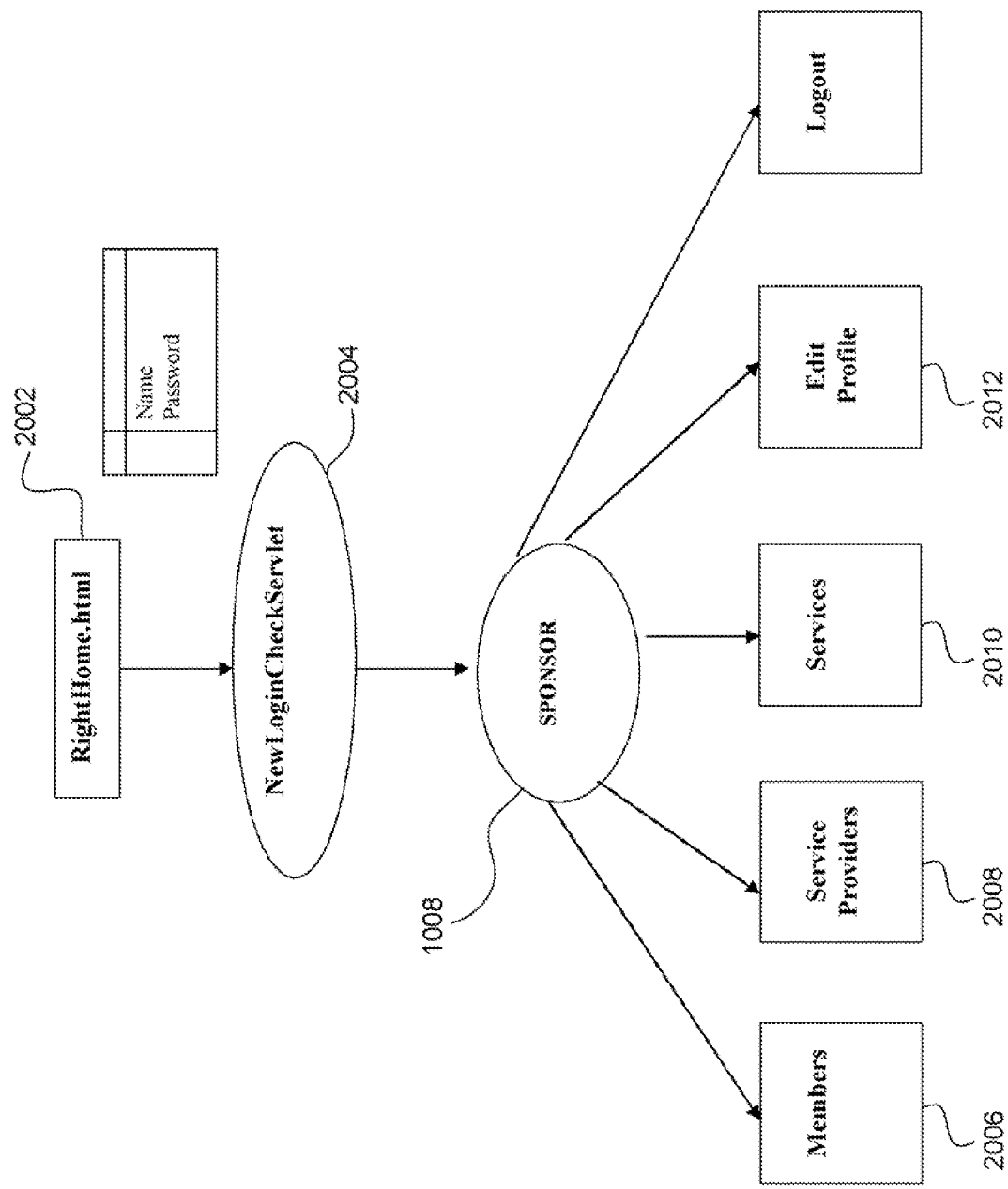
FIG. 20 depicts a Sponsor module of the system shown in FIG. 10.

FIG. 20 depicts the Sponsor Module 1008 of the system. During login, a screen 2002 is displayed. All data entered in the HTML form on this screen, i.e. name and password, goes to a login servlet 2004. This information is matched with information in a database and if it matches, a ClientType is assigned to it. If the ClientType is "sponsored" or "Sponsoror" the user is given a GroupId from the profile using the name, which is them stored in the session.

The Members submodule 2006 includes a servlet that displays disabled members. Input to this servlet includes:
  Session Name—indicates user LoginId
  Session ClientType—Indicates user Type Another servlet displays enabled members. Input to this servlet includes:
  Session Name—indicates user LoginId
  Session ClientType—Indicates user Type Yet another servlet enables or disables members. Five parameters are passed to this servlet from the previous two servlets:
  Count—this is total no of checked check boxes for enabling or disabling.
  Act—This specifies either Enable or Disable
  ClientType—Specifies member Type
  Enable+counter—This is for the name of member which are going to be enabled or disabled. The counter is a number which specifies the name as Enable1, Enable2, etc. and holds the values of member names.
  C+counter—This is for check box names. The counter is a number, so names of check boxes are C1, C2, etc. and their values are either "on" or "off".

A further servlet displays profile of members. Input to this servlet includes:
  Name—LoginId of that particular member
  ClientType—Specifies client type The Service Providers submodule 2008 includes a servlet that displays all service providers with an option to subscribe/unsubscribe. This includes a search facility. Another servlet asks for confirmation before a service provider is subscribed or unsubscribed. Yet another servlet adds or deletes a record from a registration database.

The Services submodule 2010 includes a servlet that displays subscribed services and service providers, a servlet that displays the profile of the service provider/client, and a servlet that displays members coming under a service provider for a particular service.

The Edit Profile submodule 2012 includes a servlet that allows a sponsor to modify his profile information, and a servlet that updates modifications to the profile database.

Figure 21:
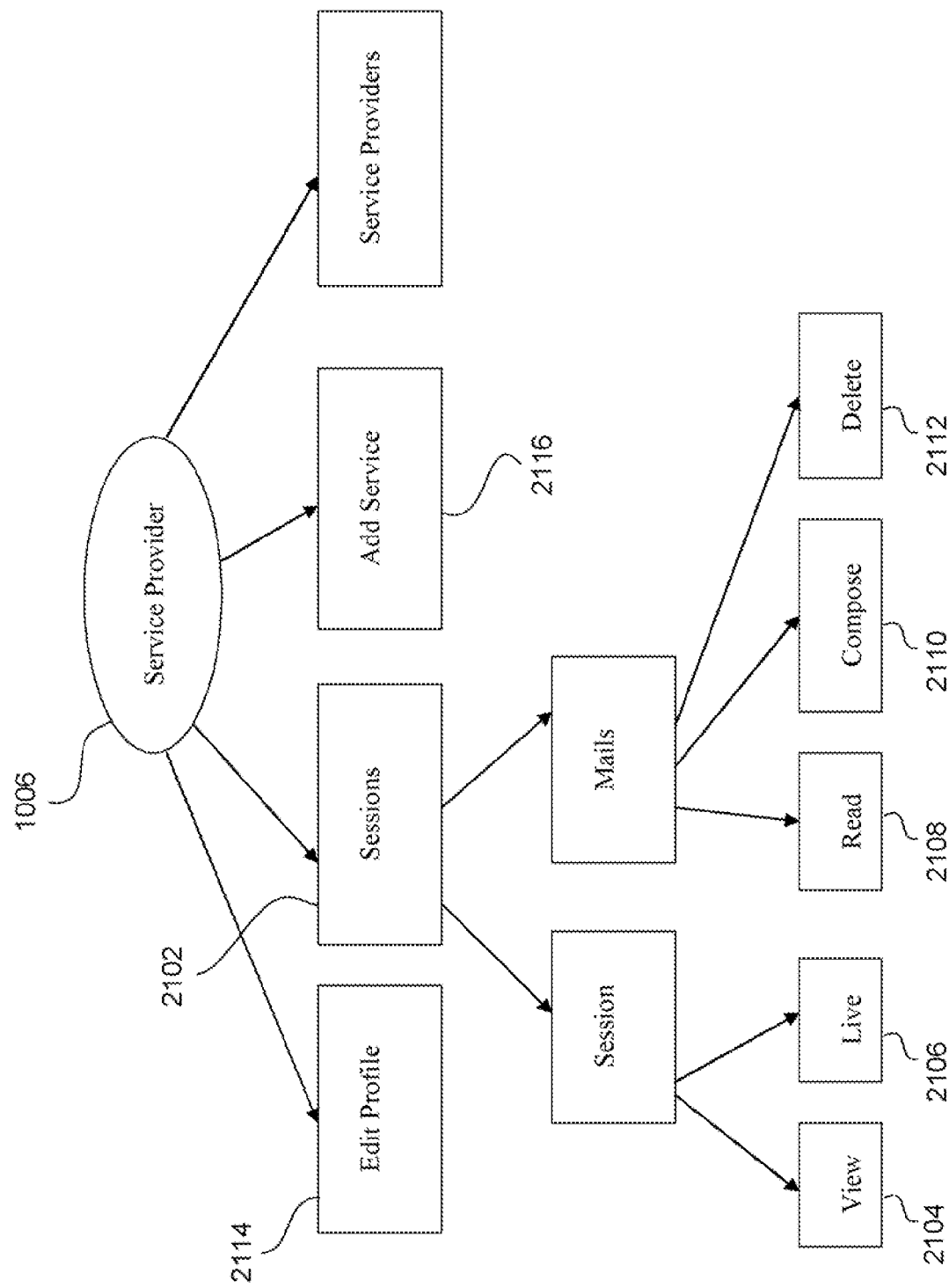
FIG. 21 depicts a Service Provider module of the system shown in FIG. 10.

FIG. 21 depicts the service provider module 1006 of the system. The Sessions submodule 2102 includes a servlet that displays services being provided and clients coming under each service. It has search facility and by default it shows only those with new messages/sessions. The Session View submodule 2104 includes a servlet that enables a service provider to view sessions sent by his/her clients, a servlet that enables a service provider to read attachment sent with session, and a servlet that launches an applet which shows the client's (patient's) vital information.

The Session Live submodule 2106 includes a servlet that enables a service provider to view bio-medical information of his client when the client is online. An animated gift indicates that the client is online. Basically this launches an applet with a filename and registration number as a parameter. The registration number is used to check authentication of each block being received.

The Mails Read submodule 2108 includes a servlet that displays mails sent by Clients, and a servlet that reads mails sent by clients and updates the read flag in the mail database. The Mails Compose submodule 2110 includes a servlet that enables a service provider to compose mails, and a servlet that writes to the mail database. The Mails Delete submodule 2112 includes a servlet that displays mails sent by Service Provider with an option to delete, a servlet that reads mails sent by a service provider, and a servlet that deletes mails sent by a service provider from the mail database.

The EditProfile submodule 2114 includes a servlet that allows a service provider to modify his profile information, a servlet that updates modifications to the profile database, a servlet that allows a service provider to modify his professional information, and a servlet that updates modifications to the therapy database.

The Add Service submodule 2116 includes a servlet that allows a service provider to add more services, and a servlet that updates the therapy database with the added service of the service provider.

The following table contains the user profile information as stored in a database of the system according to an illustrative embodiment. As soon as any user signs up with the system, a record is created. The field GroupId can contain under which sponsor the client has been registered in the case of sponsored client.

TABLE 1

(Profile)

| Column | Type | KEY |
|---|---|---|
| Name | Varchar | PRI |
| Password | Varchar | |
| FirstName | Varchar | |
| MiddleName | Varchar | |
| LastName | Varchar | |
| CompanyName | Varchar | |
| CompanyCode | Varchar | |
| ClientType | Varchar | |
| Enabled | Varchar | |
| Address | Varchar | |
| City | Varchar | |
| State | Varchar | |
| Pin | Varchar | |
| Country | Varchar | |
| Phone | Varchar | |
| Email | Varchar | |
| Website | Varchar | |
| GroupId | Varchar | |
| Authority | Varchar | |
| AuthorityEmail | Varchar | |
| LoginDate | DateTime | |
| Fax | Varchar | |
| Gender | Varchar | |
| Education | Varchar | |
| Title | Varchar | |
| Age | Varchar | |
| Address2 | varchar | |

Table 2 contains the registration details of each client with the service provider for a particular service.

TABLE 2

(Registration)

| Column | Type | KEY |
|---|---|---|
| ServiceProviderName | Varchar | PRI |
| ClientName | Varchar | PRI |
| Therapy | Varchar | PRI |
| LiveStatus | Varchar | |
| GroupId | Varchar | |
| RegNo | Int | |

Table 3 stores the details of sponsor registration with a service provider.

TABLE 3

| Column | Type | KEY |
|---|---|---|
| Sponsor | Varchar | PRI |
| ServiceProviderName | Varchar | PRI |
| Therapy | Varchar | PRI |

Table 4 stores login detail information of each user.

TABLE 4

(Login Details)

| Column | Type | KEY |
|---|---|---|
| LoginId | Varchar | PRI |
| LoginTime | DateTime | PRI |
| LogoutTime | DateTime | |
| IPAddress | Varchar | |
| LoginStatus | Varchar | |

Table 5 stores all the services.

TABLE 5

(Service)

| Column | Type | KEY |
|---|---|---|
| ServiceName | Varchar | PRI |

Table 6 contains the information on various service providers and their services.

TABLE 6

(Terapydb)

| COLUMN | Type | KEY |
|---|---|---|
| ServiceProviderName | Varchar | PRI |
| Service | Varchar | PRI |
| ServiceDescription | Blob | |
| ServiceLink | Varchar | |

Table 7 stores patient mail information.

TABLE 7

(Maildb)

| COLUMN | Type | KEY |
|---|---|---|
| Sender | Varchar | PRI |
| Receiver | Varchar | PRI |
| Therapy | Varchar | PRI |
| MailId | Varchar | PRI |
| MailDate | DateTime | |
| MailSubject | Varchar | |
| MailContents | Blob | |
| MailReadFlag | Varchar | |

Table 8 stores patient session information.

TABLE 8

(Sessiondb)

| COLUMN | Type | KEY |
|---|---|---|
| Sender | Varchar | PRI |
| Receiver | Varchar | PRI |
| Therapy | Varchar | PRI |
| SessionId | Int | PRI |
| SessionDate | DateTime | |
| SessionSubject | Varchar | |
| SessionContents | Varchar | |
| SessionReadFlag | Varchar | |
| Session_VideoPointer | Varchar | |
| Session_VoicePointer | Varchar | |
| Session_BioviewPointer | Varchar | |

Applications

The system described above can be adapted for many types of applications. Following are several exemplary WAN-based solutions, including several for monitoring various medical conditions. None that this list of applications is presented by way of example only, and is by no means exhaustive.

Urinary Incontinence (UI)

According to the U.S. Department of Health and Human Services, urinary incontinence (UI), or the unintentional loss of urine, is a problem for more than 13 million Americans, 85% of which are women. The urine loss can range from slight leakage of urine to severe, frequent wetting. This problem has severe economic and psychosocial consequences, and occurs in people of all ages, but it is especially common in older people. UI is not a natural process of aging, but rather an indication that the pelvic floor and/or the sphincters that control the process of urination may be weakening.

Traditional treatment for UI has consisted of pharmacological therapies to improve incontinence medically, and surgical therapies to treat specific anatomical problems. However, less invasive techniques such as behavioral therapy, and pelvic muscle rehabilitation have been quite successful in improving pelvic muscle tone.

One modern type of treatment is to isolate, train and strengthen the pelvic floor without recruiting any other peripheral muscles. The strength of muscular contractions is monitored using surface electromyography. This form of therapy provides immediate auditory or visual information to the person about the status of the pelvic muscle function, and has proven to be helpful in 8 out of 10 people. By monitoring the electromyography, a provider can determine whether pelvic exercises are being done correctly.

The system can be adapted to compliment any existing incontinence program. The surface electromyography signal processing unit, such as J&J Engineering's 1330 C-2 and mini C2 series; and Thought Technology's Myotrac, Procomp+, and Procomp2, plugs into the computer's serial port. Data collected by the unit is processed by the system to provide real-time medical monitoring, summary reports, statistical calculations, and visual displays, which can further be tailored for the healthcare provider's particular needs, and can each be tailored for a particular protocol. This unique technology allows healthcare providers to remotely manage clients worldwide, while communicating with them, and simultaneously viewing their real-time physiological data.

The system can easily provide customized on-line educational segments, and provide nutritional and voiding diaries made available to clients, which can be stored for review and analysis by a healthcare provider. All sessions can be securely stored with a patient and provider logon ID for retrieval and data analysis at anytime and from anywhere. The healthcare provider is able to review each session, including home practice exercises, which assures compliance and proper muscle recruitment. Real-time, stored physiological data and client's medical history can also be securely shared with colleagues for on-line consultation.

The system can also be adapted to make such specialized treatment available worldwide via the Internet, by allowing the provider to use his existing protocol to treat patients in another state or country, while simultaneously communicating with them, and viewing their real-time physiological data.

During an exemplary remote session, as with an in-office visit, the client inserts her own vaginal sensor. The sensor connects to a device that plugs into the serial or USB port of the computer. The client logs on to the main system website with a secure ID and password. A session is created.

The rest is handled by the healthcare provider who is notified with a flashing "live" button when a client is ready to begin. By clicking this button, a healthcare provider is first prompted with an impedance check to ensure a good connection.

After verifying the signals, the healthcare provider can begin a session. Auditory and visual cues guide the client through the entire protocol, and the gain can be remotely adjusted for optimal display. Both parties can communicate with built-in instant messaging features, or an external audio or visual device.

At the end of a session, the healthcare provider views a graphical and statistical summary report that includes a field for adding clinical notes. This may also be displayed on the client's end, which can even be remotely printed. All sessions are dated and stored for retrieval by either party at a later date.

Vulvodynia

Vulvodynia literally means pain in the vulva. It is a syndrome of unexplained vulvar pain that is frequently accompanied by physical disabilities, limitation of daily activities (such as sitting and walking), sexual dysfunction and psychological disability. The typical patient is in her 20s or 30s, and is frequently misdiagnosed. In a general gynecologic practice population, the prevalence of this condition may be as high as 15 percent. It is characterized by itching, burning, stinging or stabbing in the area around the opening of the vagina. Pain can be unprovoked, varying from constant to intermittent, or occur only on provocation such as attempted sexual intercourse, a condition also known as vulvar avestibulitis syndrome or vestibulodynia.

Conventional medicine often prescribes tricyclic antidepressants, while other forms of treatment consist of topical vaginal cream, intralesional interferon injection, low-oxalate diet, and physical therapy to train the pelvic floor muscles.

Pelvic floor muscle instability is a critical factor in pain associated with vulvar vestibulitis syndrome. The use of a highly sophisticated muscle measurement technology known as surface electromyography used in conjunction with an exercise program significantly stabilizes the pelvic floor muscles, reducing and, in some cases, eliminating symptoms of vulvar vestibulitis syndrome.

It has recently been discovered that the muscles of the pelvic floor in vulvodynia patients were abnormal. This abnormality can be measured by surface electromyography. Once the patients' exact abnormality is known, it can be corrected by an individual program of muscle rehabilitation and continued monitoring to assure that the correct changes occur in the muscle.

The system can be customized to provide an Internet-based software program for the new treatment protocol used in the assessment and treatment of vulvodynia. This innovative approach greatly improves patient access to the specialized treatment.

Patients experiencing vulvodynia can visit their local physicians for remote assessment and treatment by the remotely located provider. Patients would simply insert a vaginal sensor, which connects to a surface electromyographic signal processing unit that plugs into a computer's serial port. The rest is handled by the system's Internet browser-based software that allows the remote provider, and other healthcare providers, to remotely view their patient's real-time physiology, while communicating with each other using real-time audio, video, and/or text communication.

Figure 22:
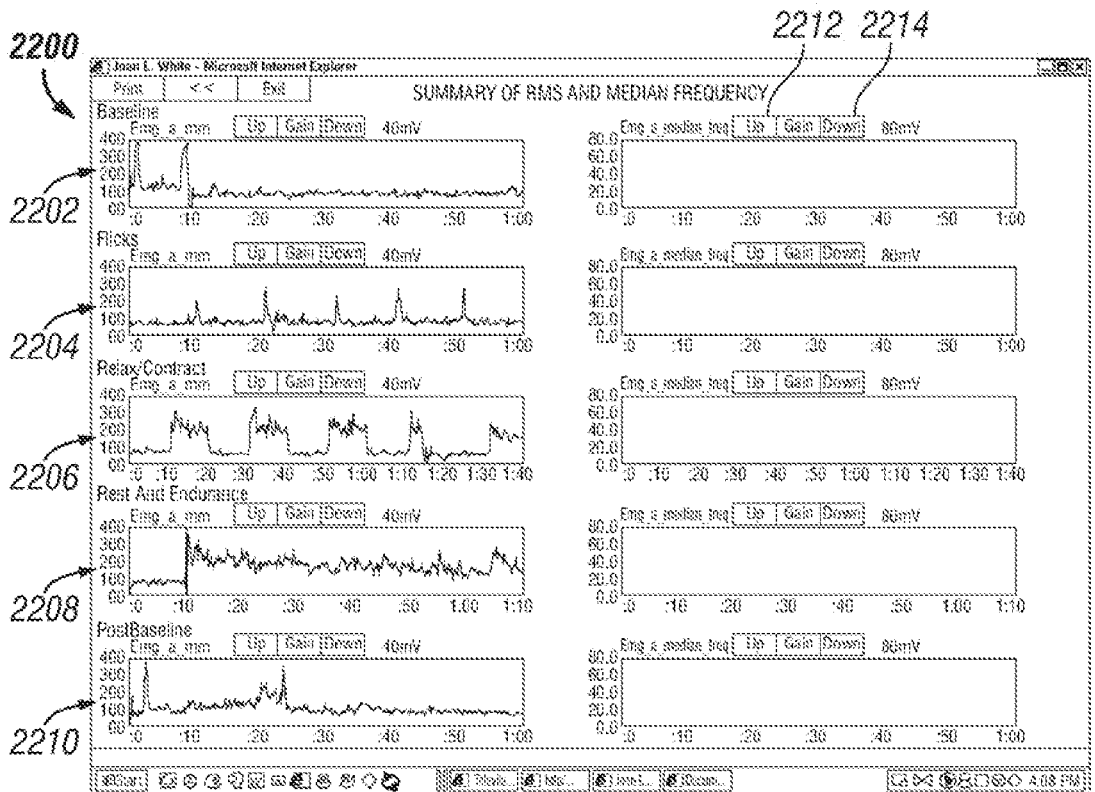
FIG. 22 depicts an illustrative graphical report of data received from a patient-side EMG device.

FIG. 22 depicts an illustrative graphical report 2200 of data received from a patient-side EMG device. The data used to generate the graphs can be received and displayed in real time, or taken from a database where the biometric data has been stored. Note that similar charts could each be presented on an individual screen.

As shown in FIG. 22, a window 2202 displays baseline readings over time. Another window shows readings during flicks 2204. Another window 2206 shows readings for during a series of contractions and relaxations. Yet another window 2208 shows readings during a rest and endurance session. A further window 2210 shows post base line readings. In each of these windows, the gain may be remotely adjusted in real time by selection of buttons 2212 and 2214.

Figure 23:
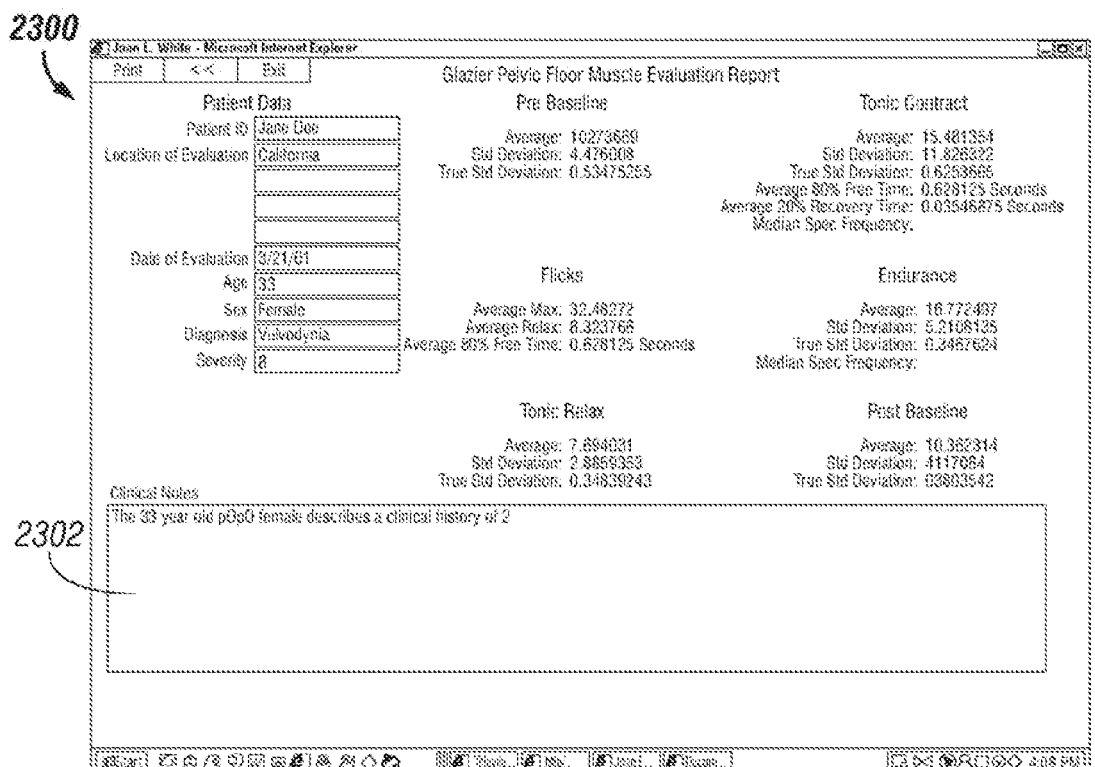
FIG. 23 shows an exemplary evaluation report showing statistic analysis of EMG data.

FIG. 23 shows an evaluation report 2300 showing statistical analysis of the data. As shown, patient data may be stored, and a field 2302 for clinical notes is provided.

Auditory and visual cues guide the patient through the assessment, while healthcare providers have complete remote control to make necessary screen adjustments. After conducting a real-time session, the remote provider is able to remotely print a statistical report for the local physician that includes clinical notes and treatment recommendations. All sessions are securely stored for retrieval and data analysis at anytime and from anywhere.

Repetitive Strain Injury (RSI)

RSI is a term used to describe a broad class of disabling pain injuries, such as Carpal Tunnel Syndrome and Tendonitis, which affect people's ability to work and perform daily activities. RSI is usually caused by a mixture of poor ergonomics & posture, stress, and repetitive motions. According to the Occupational Safety and Health Administration (OSHA), 1.8 Million workers had musculo-skeletal injuries related to ergonomic factors in 1999 alone. This included all injuries related to repetitive motion, overexertion or awkward posture. Approximately 600,000 employees missed some work because of it. Approximately $15-20 billion is spent annually for workers' compensation claims and an additional $30-40 billion is spent on other expenses such as medical care.

The system can be adapted to provide the following model for RSI specialists, who can perform assessment, treatment, and management of RSI over the Internet.

For example, a specialist, after receiving a referral, takes a medical history using web-based assessment inventories, and decides if treatment will be beneficial. Following this evaluation, a two channel EMG device is sent to the client, and an online appointment is scheduled. The client logs into the specialist's web-site and plugs the EMG device into their serial port. The specialist receives notification that his client is on line and that the device is working properly. Using a telephone, an audio/video conferencing software, the specialist directs the client through the exercises designed to bring about changes in the clients muscle activity, as displayed on the computer monitors. The specialist views the muscle activity, as recorded from the EMG device, in real-time allowing him to direct the treatment session remotely. At the end of the appointment, the patient is given practice exercises, which the patient conducts on his own using the EMG device. The practice sessions may be saved for the specialists to review anytime from anywhere to track the patient's progress.

Management of Pulmonary Disorders

Millions of Americans suffer from pulmonary disease while clinicians are unable to monitor their disease-state progression on a day-to-day basis, or between office visits. Patients do not always have easy access to healthcare or the ability to visit specialists because of their location.

Figure 24A:
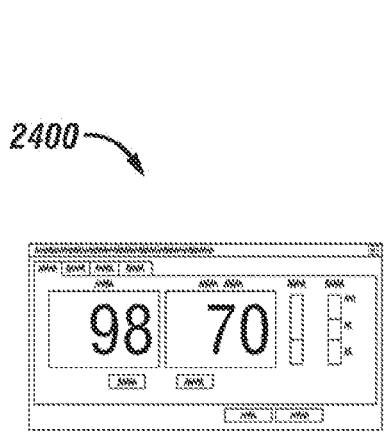
FIG. 24A shows an illustrative screen displaying a patient's blood oxygen saturation and pulse rate.
Figure 25:
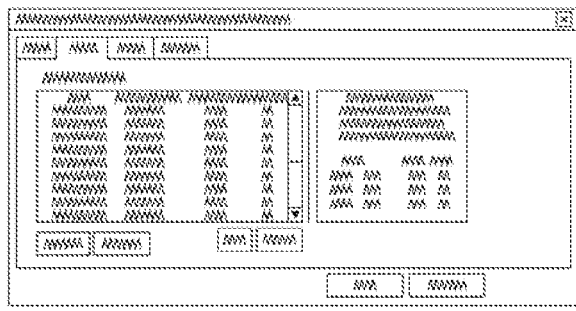
FIG. 25 depicts an illustrative screen displaying a comprehensive report of a pulse oximetry testing session.
Figure 26:
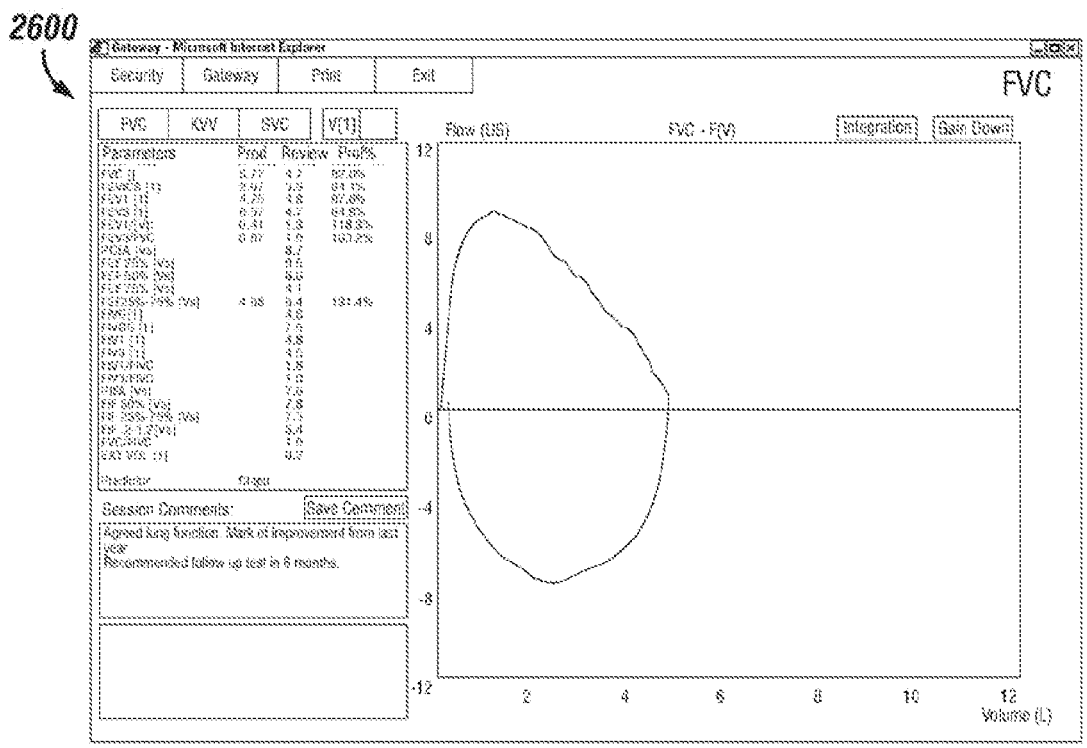
FIG. 26 depicts an exemplary screen displaying a spirometry graph, numerical results, and predictors.
Figure 24B:
FIG. 24B depicts another screen displaying historical blood oxygen saturation and pulse rate data.
Figure 24C:
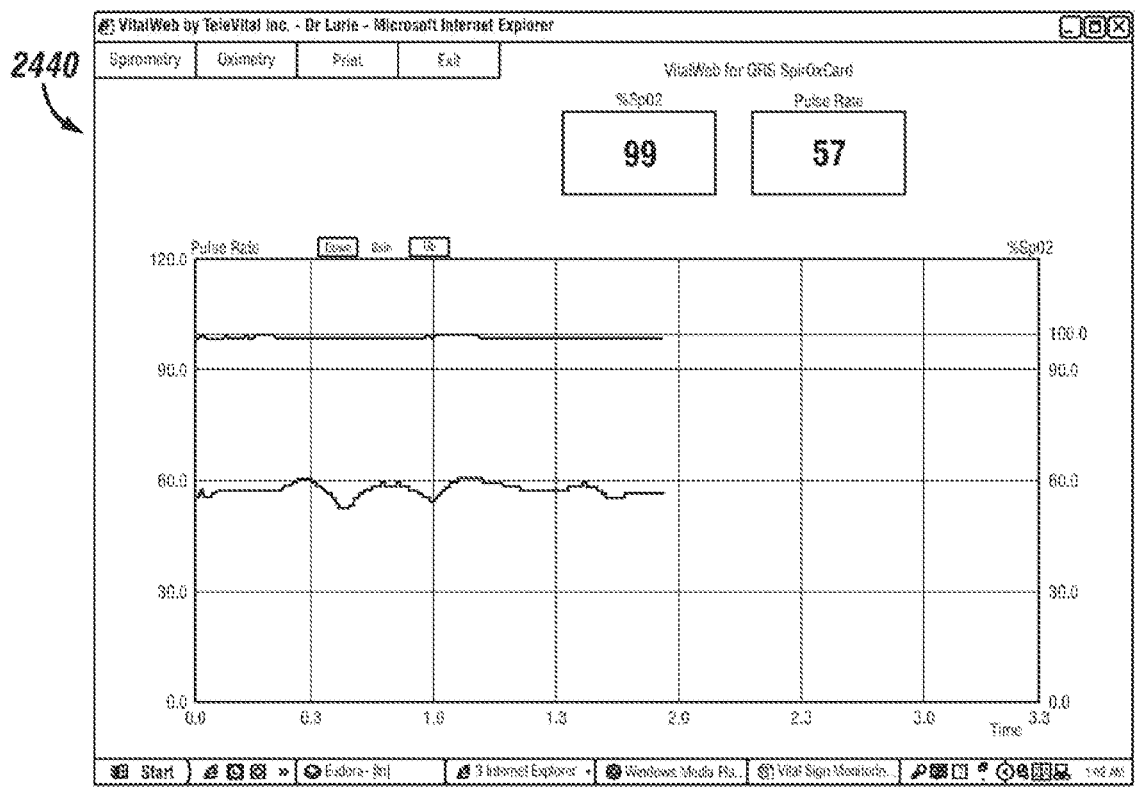
FIG. 24C shows a screen displaying both historical and numerical oximetry data.

The system may be adapted to include web-enabled spirometers and oximeters, allowing healthcare practitioners to perform remote spirometry and oximetry tests. FIG. 24A shows a screen 2400 displaying a patient's blood oxygen saturation and pulse rate. FIG. 24B depicts another screen 2420 displaying historical blood oxygen saturation and pulse rate data. FIG. 24C shows a screen 2440 displaying both historical and numerical oximetry data. FIG. 25 depicts a screen 2500 displaying a comprehensive report of a pulse oximetry testing session. FIG. 26 depicts a screen 2600 displaying a spirometry graph, numerical results, and predictors.

Web-enabled spirometry allows for real-time remote testing, retrieval, and analysis of a patient's pulmonary function tests from any Internet-enabled computer. Such remote spirometry greatly improves the management and prevention of pulmonary problems in various healthcare segments, including pharmaceutical research, HMO's, education institutions, and from isolated areas such as on aircrafts and ships.

The system's web-enabled protocols support multiple devices, and offer bi-directional communication, while supporting multimedia features. Further, the system's customizable display screens, summary reports, statistical calculations, history intake forms, and on-line educational segments can be tailored for a specific protocol.

The system's web-enabled devices allow physicians a way to provide better services to their parents, while allowing them to get reimbursed for their time. As a further benefit to the remote provider, fee-for-service pulmonary interpretations, education, and treatment protocols can be offered to other healthcare providers.

Cardiovascular Diseases (CVD)

60,800,000 Americans have one or more types of CVD according to current estimates. One in five males and females has some form of cardiovascular disease. The cost of cardiovascular diseases and stroke in 2000 is estimated at $326.6 billion by the American Heart Association. This figure includes direct costs, which include the cost of physicians and other professionals, hospital and nursing home services, the cost of medications, home health and other medical durables and lost productivity resulting from morbidity and mortality (indirect costs). Congestive Heart Failure (CHF) accounts for more hospital admissions than any other diagnosis in patients over the age of 65, and accrues costs between $10 and $40 billion dollars annually according to the Health Care Financing Administration (HCFA). In 1998, the AMA estimated that over 7 million Americans receive home health care each year at a cost of $25 billion.

The web based real-time streaming of vital signs and audio/video data along with central storage and retrieval features provided by a system according to one embodiment are ideal for remote cardiac rehabilitation and cardiac monitoring for sectors like home-care, nursing homes, assisted living facilities for elders and other applications like remote health monitoring on aircraft and ships.

One system includes wireless blood-pressure devices which can measure systolic pressure continuously without the need of the inflation pumps. Taking blood pressure readings two to three times a week is extremely helpful. Some patients get nervous and their blood pressure shoots up just from coming to the doctor's office. Outside readings give physicians a better sense of blood pressure control. They can also correlate the change in the blood pressure to the activities either at their home or office. The real-time vital monitoring service in the corporate market further helps companies to retain productive personnel, while decreasing general employee absenteeism and increasing overall productivity.

Heart Disease

Coronary heart disease is a disorder that affects the heart muscle and the blood vessels. The most serious danger of coronary heart disease is a heart attack, which occurs when the supply of blood to the heart is greatly reduced or stopped due to a blockage in a coronary artery. Coronary heart disease (including heart attack) is the single largest killer in the United States accounting for one out of every 4.7 deaths. There are more than one million heart attacks each year in the US, and every year more than 400,000 people die from heart attacks.

A system according to one embodiment includes a web-enabled EKG device to provide real-time monitoring, assessment, analysis, retrieval, and storage of EKG signals over the Internet.

Figure 27:
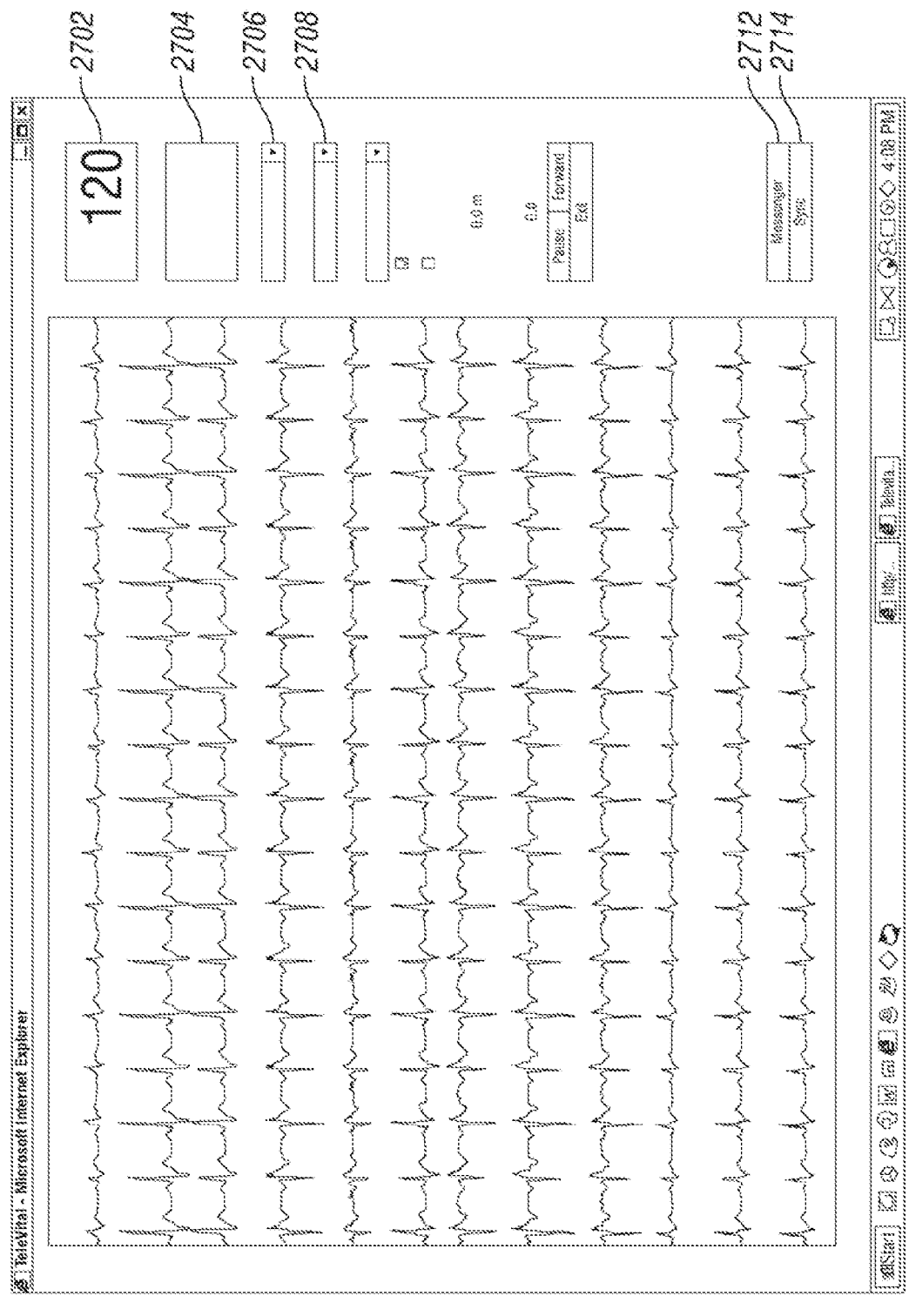
FIG. 27 depicts an exemplary screen showing real time data streaming of a 12-lead EKG.
Figure 28:
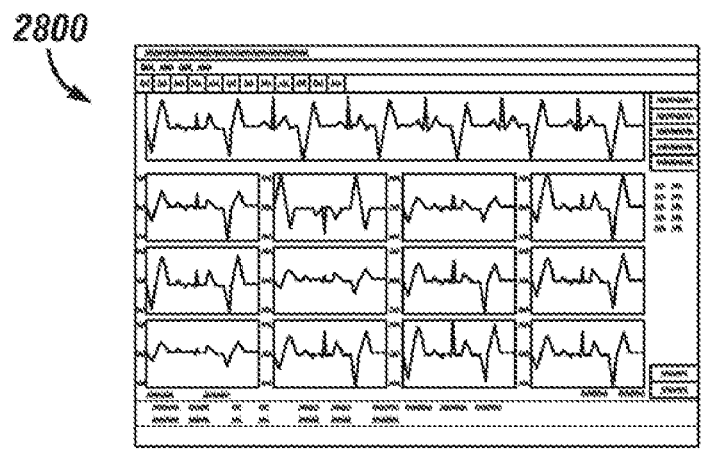
FIG. 28 illustrates another screen displaying EKG data.

FIG. 27 depicts a screen 2700 showing real time data streaming of a 12-lead EKG. The heart rate is shown in window 2702. The calibration pulse is shown in FIG. 2704. Sensitivity, speed selections, and lead selections may be set and changed in real time via menus 2706, 2708, 2710, respectively. Options can be provided for grids and calipers. Snap shots of the data may be created, reviewed, and annotated from this screen. Further, the data may be paused, printed and searched. Instant messaging is enabled by selecting button 2712. Also, remote control and synchronization functions are accessible by selecting button 2714. FIG. 28 illustrates another screen 2800 displaying EKG data.

Figure 29:
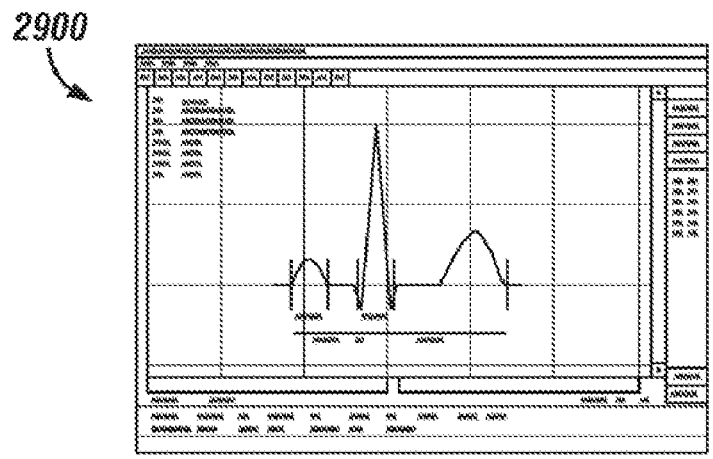
FIG. 29 shows an illustrative screen displayed upon zooming in on an EKG waveform.
Figure 30:
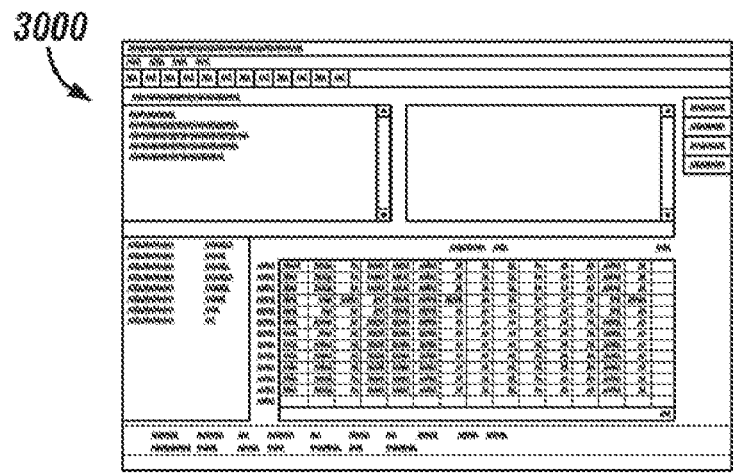
FIG. 30 depicts a details screen displaying interpretation comments and measurements for an EKG.

The system instantly performs a series of measurements and provides a complete narrative interpretation. FIG. 29 shows a screen 2900 displayed upon zooming in on a waveform. FIG. 30 depicts a details screen 3000 displaying interpretation comments and measurements for the EKG. Further, the waveforms and reports can be printed.

Benefits to manufacturers of EKG devices include allowing the manufacturers to provide remote demonstrations of their products, remote product support, and analysis of device usage. Manufacturers may also be able to provide immediate software upgrades without the software distribution through CDs.

Remote Management of Heart Disease

Hundreds of billions of dollars are lost each year because clinicians are unable to monitor disease-state progression on a day-to-day basis, or between clinic visits. Patients don't always have easy access to healthcare or the ability to visit specialists because of their location. There is a great need for telehealth technologies in homecare and ambulatory settings as outpatient disease management handles roughly one hundred million chronic patients in the US alone.

The system according to one embodiment can include a web-enabled QRS Diagnostic's EKG card, which allows healthcare practitioners the ability to perform remote diagnostic procedures in real-time over the Internet. The web-enabled solution allows for central storage, retrieval, and analysis of EKG signals in remote cardiac rehab and cardiac monitoring sectors such as homecare, nursing homes, assisted living facilities. HMO's, emergency care and from isolated locations such as aircrafts and ships.

Fee-for-service EKG interpretations, education, and treatment protocols can be offered to other healthcare providers.

Stroke and Blood Pressure

Inadequately managed blood pressure may be responsible for one third of strokes in patients who are being treated pharamcologically for hypertension, suggest results of a recently published study on Strokes. The numbers are startling: every 53 seconds someone in the United States suffers a stroke, and someone dies from one every 3.3 minutes. Strokes affect a half million people each year, killing about a third of them and disabling another 200,000, according to the American Stroke Association, a division of the American Heart Association. Taking readings two to three times a week is extremely helpful. For one thing, some patients get nervous and their blood pressure shoots up just from coming to a doctor's office. Outside readings give physicians a better sense of blood pressure control. The system may include a wireless continuous blood pressure monitor that is easy to wear and does not need the pumps.

Attention Deficit Hyperactivity Disorder (ADHD)

ADHD is the most commonly diagnosed behavioral disorder of childhood, estimated to affect 3 to 5 percent of school-age children. As many adults as children also have the disorder as it generally remains into adulthood. There is no cure, only a toxic medication to mask the symptoms. The National Institute of Mental Health says that at least 800,000 school-age children have attention disorders. Its core symptoms include developmentally inappropriate levels of attention, concentration, activity, distractibility, and impulsivity. Children with ADHD usually have functional impairment across multiple settings including home, school, and peer relationships. ADHD has also been shown to have long-term adverse effects on academic performance, vocational success, and social-emotional development. One of the major controversies regarding ADHD concerns the use of psychostimulants to treat the condition because of adverse side effects and potential overuse and abuse of drugs like Ritalin, Dexedrine and Cylert. Medications do not treat the condition, only mask the symptoms.

As an alternative to medication, some neurofeedback specialists and neurologists are using EEG signals for the assessment and treatment of ADHD with the help of real-time monitoring.

The system according to one embodiment provides an Internet based infrastructure for Neurofeedback specialists and neurologists to remotely monitor, manage and treat ADD and ADHD patients with the following model.

Following an in house or online evaluation of an ADD or ADHD child, a treatment regimen is designed, and programmed into the child's electronic file on the Internet. The child is sent home with a fashionable helmet integrated with wireless EEG sensors. The treatment regimen utilizes high definition 3-D video games that respond to the attention of the children, as recorded from the EEG sensors. As the children achieve greater levels of attention, feedback is provided to the children in a way that allows them more functionality over the video game. The 'treatment' sessions are done over an Internet connection, while the brainwaves from the children are streamed, stored and analyzed in real-time by the specialists's office remotely. The specialist has the option at any time to change the training specifications. If the specialist is not available to monitor the training session, he has the ability to view all saved sessions, allowing him the option, when desired to make any changes to the treatment regimen. Remote evaluations are also conducted to document improvements.

The system compliments any existing protocol, not only by providing the infrastructure for real-time, remote physiological monitoring, but summary reports, statistical calculations, intake forms, on-line educational segments, diaries, and visual displays can all be customized for the healthcare provider's particular needs. Each session can be reviewed, including home practice exercises, which assures compliance and proper muscle recruitment. Real-time, stored physiological data and patient history can also be securely shared with colleagues for a remote consultation.

Remote Fetal Monitoring

Most pregnant women worry about the health of their unborn child, and are unsure of when to call their healthcare provider. The system according to one embodiment may include web-enable fetal monitoring devices so that fetal Doppler ultrasound can be monitored, fetal heart rate (FHR) can be recorded, and uterine contractions can be measured. Contractions can be timed from the beginning of one contraction to the beginning of the next contraction, which helps to determine true labor. Most obstetricians believe that fetal monitoring identifies serious fetal problems earlier than other methods, thus improving outcome. Physicians can evaluate this data in real-time over the Internet any time and in any place to ensure the safety of the unborn child. All data is securely stored for future retrieval and playback.

Out Patient Monitoring

Many patients require follow up by Home-Health agencies once they leave the hospital. These agencies monitor vital signs, administer medications, and keep physicians informed about the patient's condition. A system according to one embodiment may include medical devices allowing home health nurses and medical doctors the ability to remotely monitor the health of their patients, thereby reducing or eliminating the need for home visits by medical personnel or office calls by the patients.

Hemodialysis

This is the most prevalent form of renal replacement therapy for patients with end stage renal disease (ESRD) and is typically performed 3 days per week for 3.5 to 4 hours either at home or in a dialysis center. There are over 350,000 patients with end stage renal disease on dialysis in US, and is projected to increase by 7% per year to over 660,000 by the year 2010 according to a recent USRDS report. The economic cost of this program expected to increase from $12 billion to $28 billion by 2010. The majority of the dialysis market (60-65%) is being serviced by publicly traded health care companies, and the other (35 to 40%) is provided by hospitals and private individuals.

The process involves a dialysis machine with a lowered dialysate flow, the internal jugular catheter with newly designed locking box to prevent accidental disconnection and reverse osmosis system for water purification. This requires a remote monitoring of the dialysis functions displayed on the dialysis machine via a modem or internet connection at a nocturnal hemodialysis office. They need the continuous "live" monitoring of all the patients on a single screen. The system according to one embodiment can provide the required display of data from multiple dialysis machines by integrating the machines into the system.

Nocturnal Hemodialysis

This is a novel form of renal replacement therapy which is performed 6-7 nights per week for 8-10 hours during sleep. This form of therapy shows considerable advantages over the conventional three times a week dialysis. Daily hemodialysis is more physiologic in that it reduces the fluctuations of the level of toxic waste products. It provides hemodynamic stability even in-patients with unstable cardiovascular system. Phosphate control was better and many patients discontinued their phosphate binders. Blood pressure control can be achieved with fewer medications.

Sleep Apnea-Hypopnea Syndrome

Sleep apnea-hypopnea syndrome is characterized by repetitive episodes of upper airway obstruction that occur during sleep usually associated with reduction in blood oxygen concentration. However this definition is somewhat narrow and should include occurrence of partial reduction of airflow. This syndrome is associated with snoring, daytime sleepiness and hypertension. Monitoring approaches include the standard in-laboratory polysomnography that includes EEG, right and left electro occulogram, chin electromyogram. Breathing is monitored with thermocouples or thermistors, thoracic EMG or inductive plehysmography and oximetry. These data are collected in the lab by attended monitoring.

A system allows remote monitoring of such devices by providing in-home monitoring utilizing polysomnography and oximetry with newer portable and/or disposable devices with on line live monitoring.

Health Clubs

An embodiment provides web-enabled fitness equipment, and allows personal fitness data to be monitored, recorded, analyzed, and stored in a personal electronic fitness log. It provides an easy way for clients to keep track of their workout progress when they are at home, traveling, or at another chained health club. Trainers can monitor the activities and progress of their clients remotely. Health club administration may also be able to monitor the usage patterns of fitness equipment, and to provide remote diagnostics.

Computer-Related Discomfort (CRD)

Computer Related Discomfort (CRD) is a term used for a broad class of injuries, such as Carpal Tunnel and Tendonitis, which affect people's ability to work and perform activities of daily living. It has also been referred to as Work-related Musculoskeletal Disorders (WMSD). It is a musculoskeletal injury where soft tissues in the body, primarily muscles and occasionally nerves or tendons, become irritated and inflamed from repeated physical movements. There are a multitude of potential risk factors for RSI, however it is important to understand that not all of these factors need to be present for an injury to occur.

Due to the rise in computer use over the years, the Occupational Safety and Health Administration (OSHA) estimates that every year, between 800,000 and 2.7 million Americans develop some form of computer-related discomfort CRF, which can lead to repetitive strain injuries (RSI). CRD has signs and symptoms that develop gradually, and pain and/or discomfort may not be immediately apparent. Over time, signs and symptoms can include pain, tingling, numbness, and swelling arising from a combination of physical tension, emotional stress, repetitive motion, improper posture and ergonomics. Computer users are exposed to all of these, and are commonly prone to poor typing and mousing habits that target the more delicate muscles of the hand and wrist in particular.

One of the major factors in CRD is that some muscles may be fatiguing while other muscles are compensating or overworking. The muscles that were meant to do the work have not been functioning properly, either as a result of acute injury, or from fatigue due to long-term overuse. Over time, neighboring muscles get recruited to compensate for this injury. They quickly fatigue because they are not designed to do the job. When muscles do an unexpected task very suddenly, or when they fatigue from doing repetitive work in awkward positions without rest breaks, they can develop tight knots or bands called Trigger Points. These trigger points are the spots, which indicate that the muscle is not working properly. Trigger points can refer symptoms to certain parts of the body in very consistent ways. It is possible that most of the symptoms being experienced are the result (directly or indirectly) from trigger points. CRD has the potential to cause crippling disability and pain with gradual increments of damage.

These symptoms affect work and daily activities caused by physical and/o psychological stresses on the body beyond its ability to adapt. When muscles and tendons are overused without sufficient time for healing and repair, microscopic tearing occurs with resultant swelling and pain.

One embodiment provides standardized simple screening questionnaires and inventories that allows for the prediction of employees susceptible of developing repetitive strain injuries (RSI). There are many factors that are believed to be responsible for the development of RSI, or "Computer Related Discomfort" (CRD), and these questionnaires help to assess the factors that may contribute to the development of pain symptoms. The inventories include a quick computer related discomfort inventory which assesses pain symptoms, coping skills, work style, work behavior and ergonomic factors, work demands, stress, and interaction/interpersonal styles. Included with each questionnaire is educational content that explains how each factor may contribute to the development of CRD. Treatment and education protocols can be integrated with biofeedback devices to prevent, manage and treat the factors responsible for the development of stress and pain symptoms.

One illustrative embodiment provides a CRD questionnaire. This questionnaire is a multi-part diagnostic tool for assessing whether or not a patient currently has computer related discomfort (CRD), and can identify specific risk factors for developing CRD in the future. For each area that indicates a moderate or high risk factor, the patient will be prompted with a link to a more detailed questionnaire.

The detailed surveys are Work Behavior, Work Style, Stress, Coping Skills, and Pain Inventory. The Work Behavior survey assesses a patient's work behaviors, computer use habits, posture, and ergonomic factors that may contribute to the development of computer related discomfort.

The Work Style survey assesses a patient's particular way of handling events at work. Research has documented two work style behavior patterns that lead to more injury and disease. These work style patterns are called Type A and Type C work style behaviors. Type A patterns are characterized by time urgency, hostility, and competitiveness. Type C is characterized by passiveness, hopelessness, and suppression of emotions.

The Stress survey assesses the contribution of stress in the development of computer related discomfort. Stress has long been known to be a significant risk factor in the development of disease, injury, and illness. One area related to stress includes work demands, which assesses the influence and dynamics of work on health. High work demands are known to contribute to pain and disability. Another area is stress symptoms, which assesses the contribution of other sources of stress in a patient's life. The occurrence of stress symptoms provides cues to the possibility of experiencing stress in the patient's life.

The Coping Skills survey assesses a patient's particular way of handling events at work. People handle stress in different ways. What may be stressful to one person may not be stressful to another. It is not so much a matter of how much stress is in the patient's life, but how she handles and copes with the stress.

The Pain Inventory survey assesses a patient's pain intensity and tells whether pain affects his ability of perform his job or not. This inventory can be used to teach the patient how to handle and cope with the pain.

Figure 31:
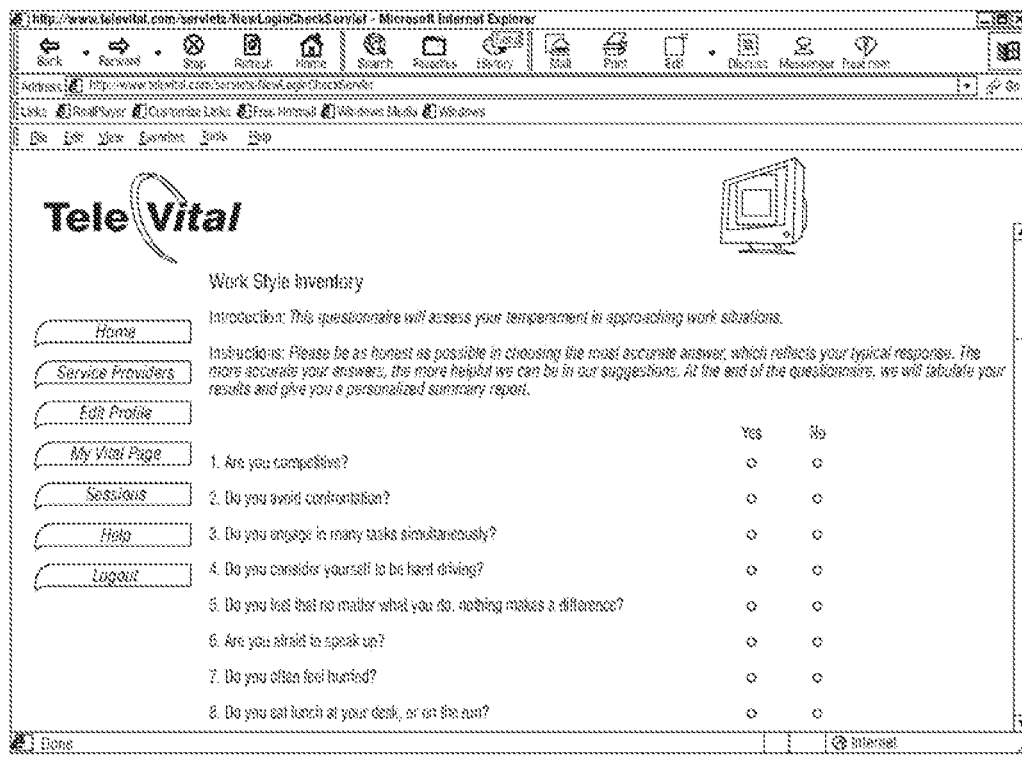
FIG. 31 is a screen shot of a Work Style survey according to one embodiment.
Figure 32:
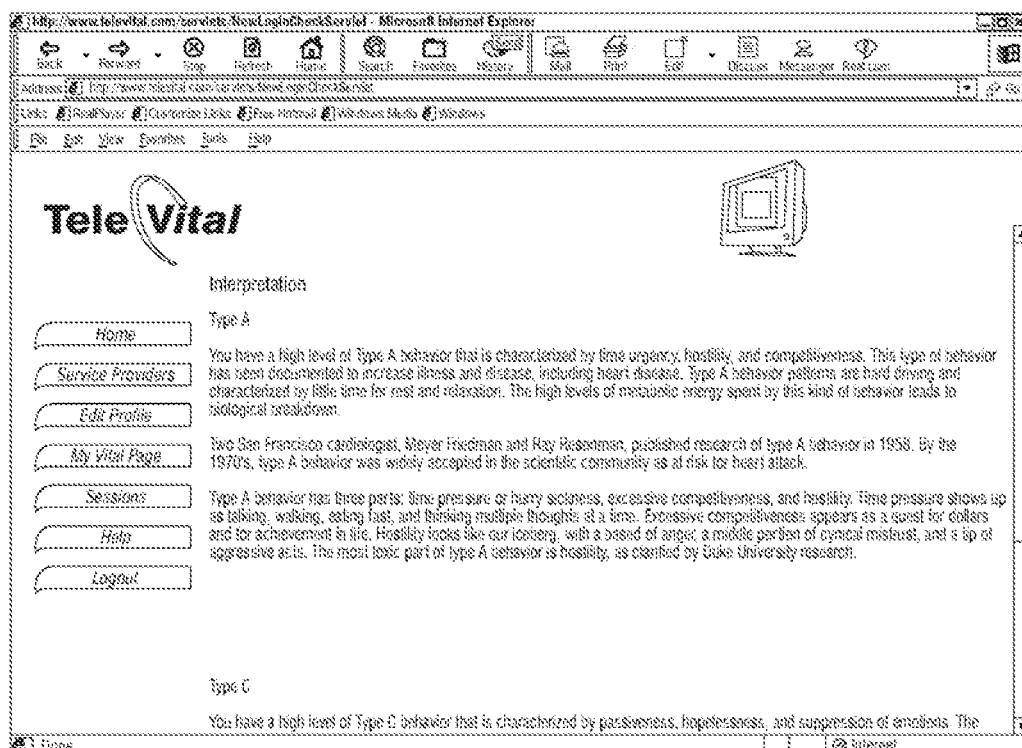
FIG. 32 shows an exemplary results screen, which provides an interpretation of the patient's work style based on answers to the survey of FIG. 31.

FIG. 31 is a screen shot of a Work Style survey 3100. The answers entered by the patient are analyzed and results are generated. FIG. 32 shows a results screen 3200, which provides an interpretation of the patient's work style. The other types of survey and results screens can be of a similar format, but would include questions pertinent to the particular objectives sought.

Figure 33:
FIG. 33 shows an illustrative CRD questionnaire results page.

FIG. 33 shows a CRD questionnaire results page 3300, showing which surveys the patient has taken, and the risk level. The patient may also access other survey pages and results of completed surveys by selecting the appropriate links.

Remote Troubleshooting

The system may also be used for remote troubleshooting. For example, a manufacturer of the client-side device can use the remote control capabilities of the system to debug and diagnose any hardware connected to the WAN. Further, device manufacturers can monitor, via the WAN, how the device is being used, and analyze any problems or limitations experienced by the providers. This will allow for the improved development software and hardware based on real time feedback received from providers. Also, support from the device manufacturers can be more readily obtained.

Product Demonstrations/Training

The system further provides for product demonstrations and sales over the WAN, reducing the need for a sales representative to visit a doctor's office. The system may also be used for remote supervision and training of local health care providers by a more experience health care provider located remotely.

Collaboration

One embodiment provides a message board that allows clinicians to share research, results, and protocols. Another message board and/or instant messaging system can be provided for patients to allow for support networks, integrated with a wide range of educational materials. Further, pages having information on treatment applications and clinician biographies may be provided on the website. This information could be posted by participating providers, as well as taken from journals, etc.

Monitoring in Remote Locations

Many patients do not even have access to adequate health care facilities. One embodiment is adapted to remote physiological monitoring of a dispersed rural population. For example, satellite or telephone communications can be used to provide healthcare monitoring in forests, tribal areas, mountainous regions, the arctic during expeditions, at sea, etc.

Figure 34:
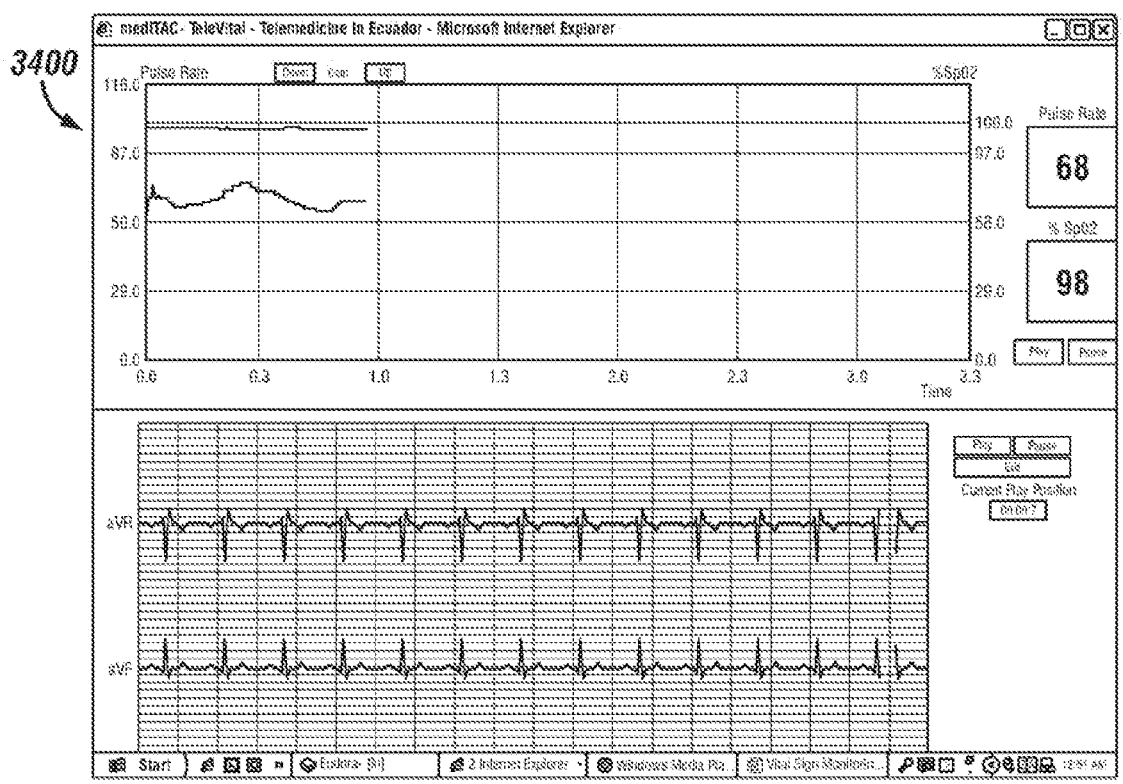
FIG. 34 depicts an illustrative screen showing anesthesiological monitoring data.

Others have access only to healthcare providers with limited knowledge. One embodiment allows local surgeons, etc. to be assisted by remote providers including specialists and anesthesiologists. For example, an anesthesiologist in the United States can remotely assist a surgeon performing surgery in Ecuador. FIG. 34 depicts an illustrative screen 3400 showing anesthesiological monitoring data. Thus, the patient can have access to the finest care possible at minimum cost. As another example, a particular hospital may not have an inhouse specialty for treating some protocols. So when the particular treatment protocol is required on an urgent or regular basis, it can be "imported" from a participating hospital.

Other Applications

Again, it is stressed that the system and methodology of the present invention contemplates uses in many applications other than those presented herein, such as post surgical monitoring; ICU (Intensive Care Unit) monitoring; remote anesthesia monitoring during a surgical process, vital sign monitoring including EKG in the ambulances and other types of vehicles, ships and airplanes; remote physiological monitoring of population exposed to bioterrorism attack; and remote monitoring at correctional facilities.

Figure 35:
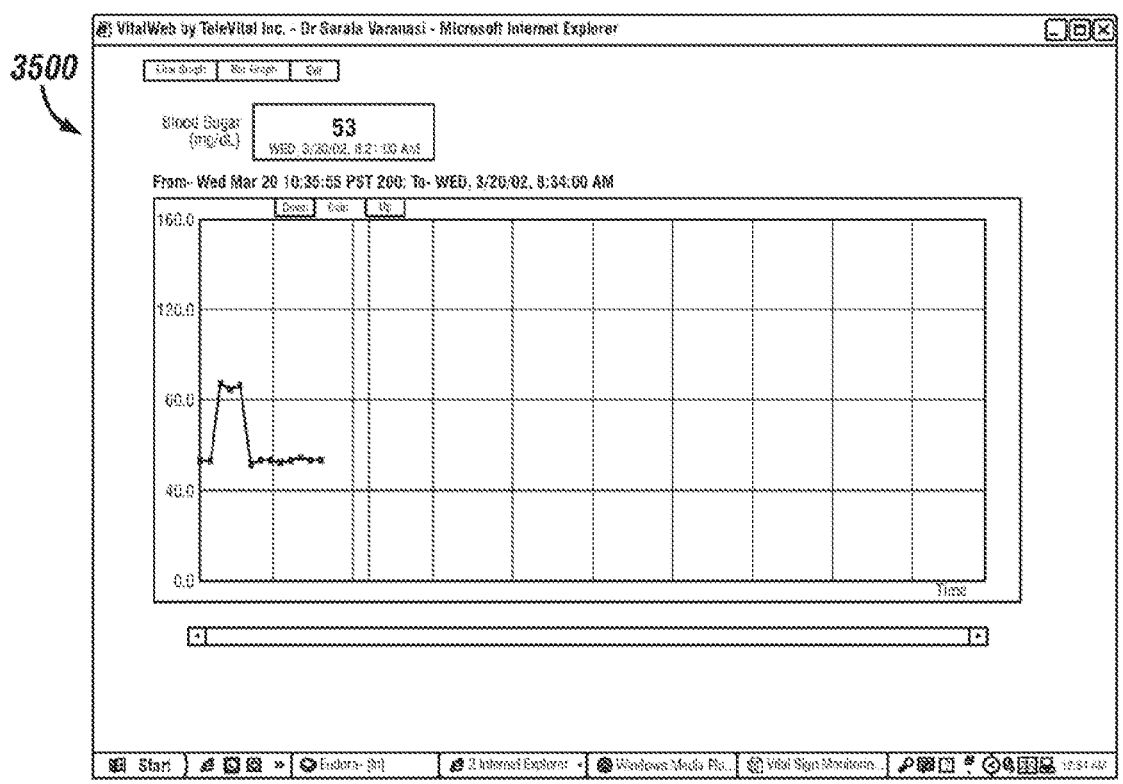
FIGS. 35 and 36 show illustrative screens displaying blood sugar monitoring data.
Figure 36:
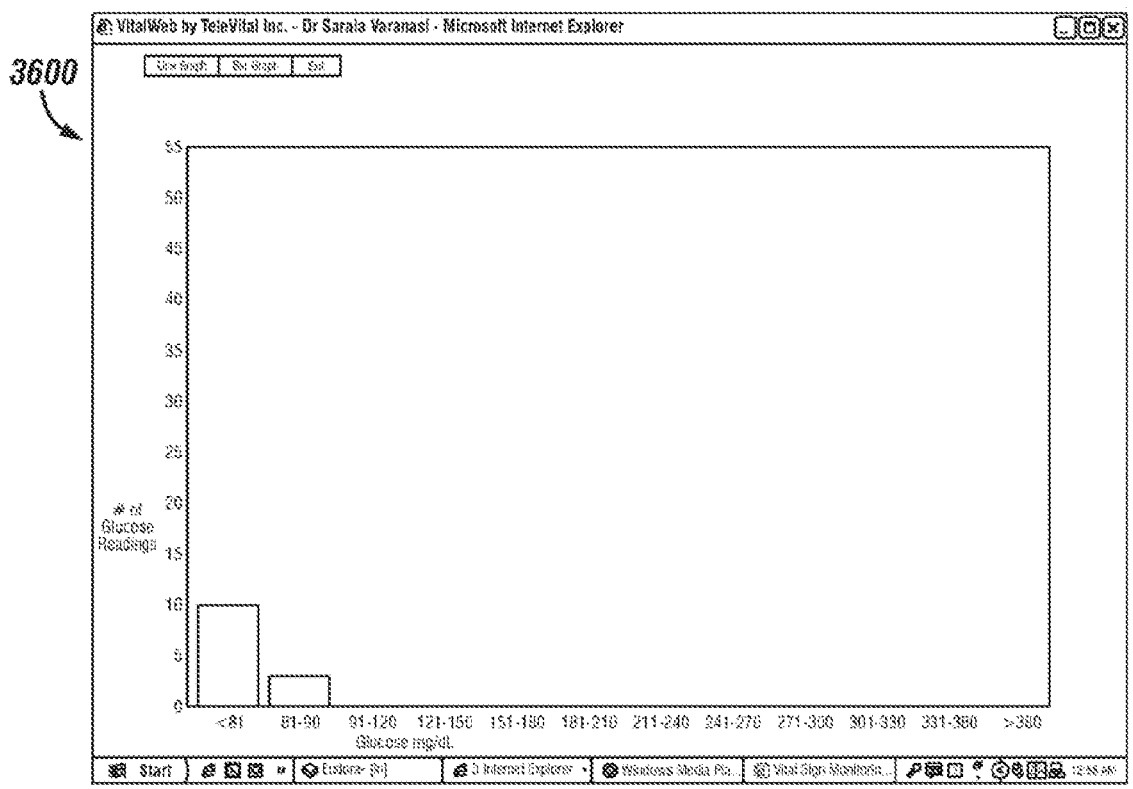
Figure 37:
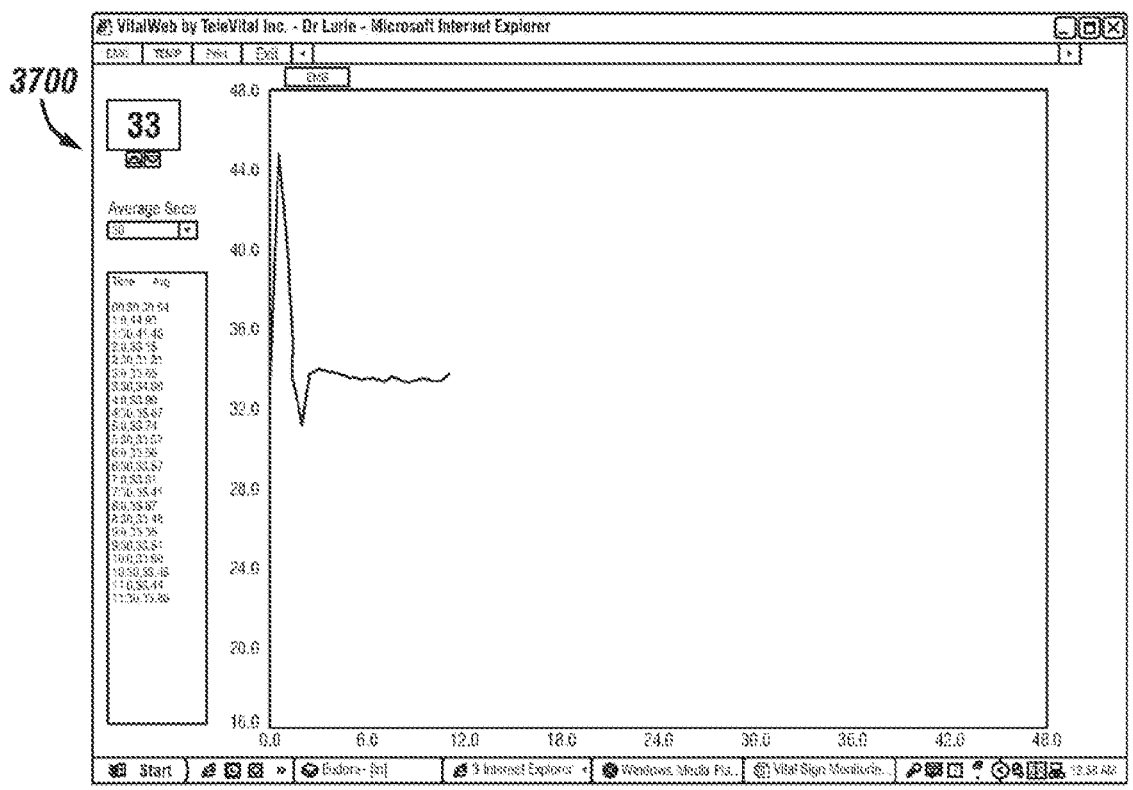
FIG. 37 depicts an exemplary screen displaying EMG monitoring data that can be used as part of a headache treatment protocol.
Figure 38:
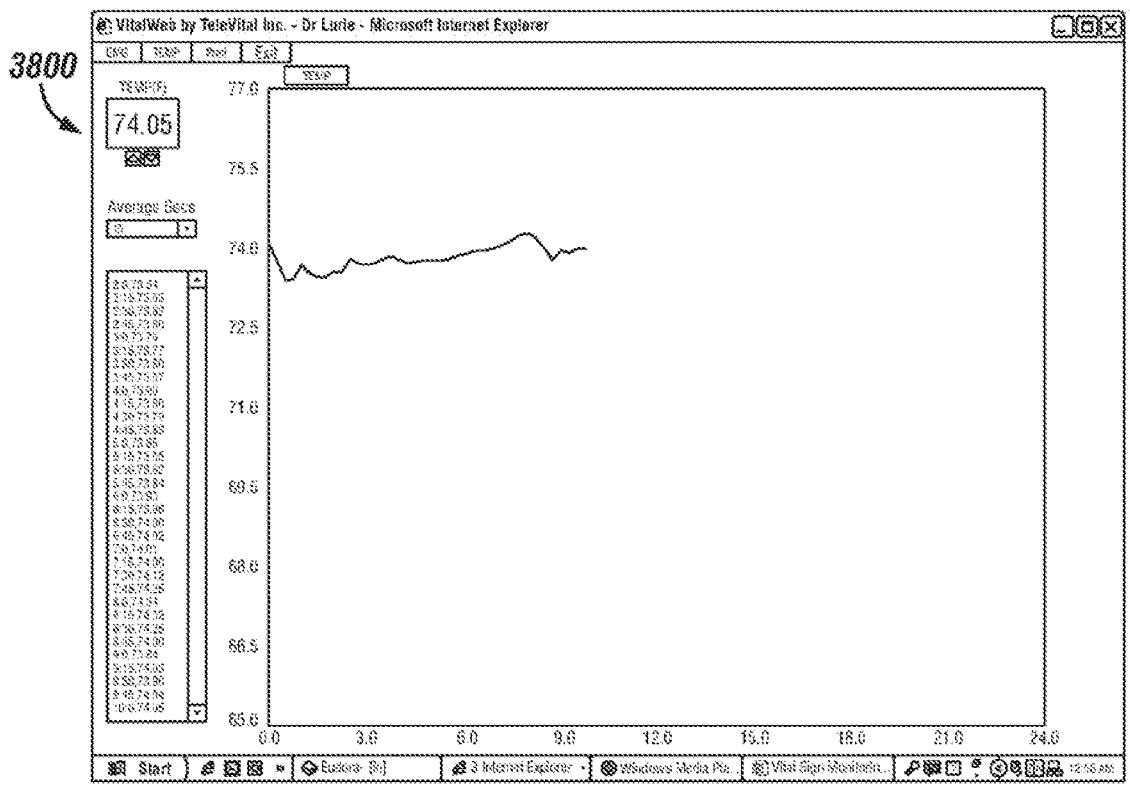
FIG. 38 depicts an illustrative screen displaying peripheral body temperature data.
Figure 39:
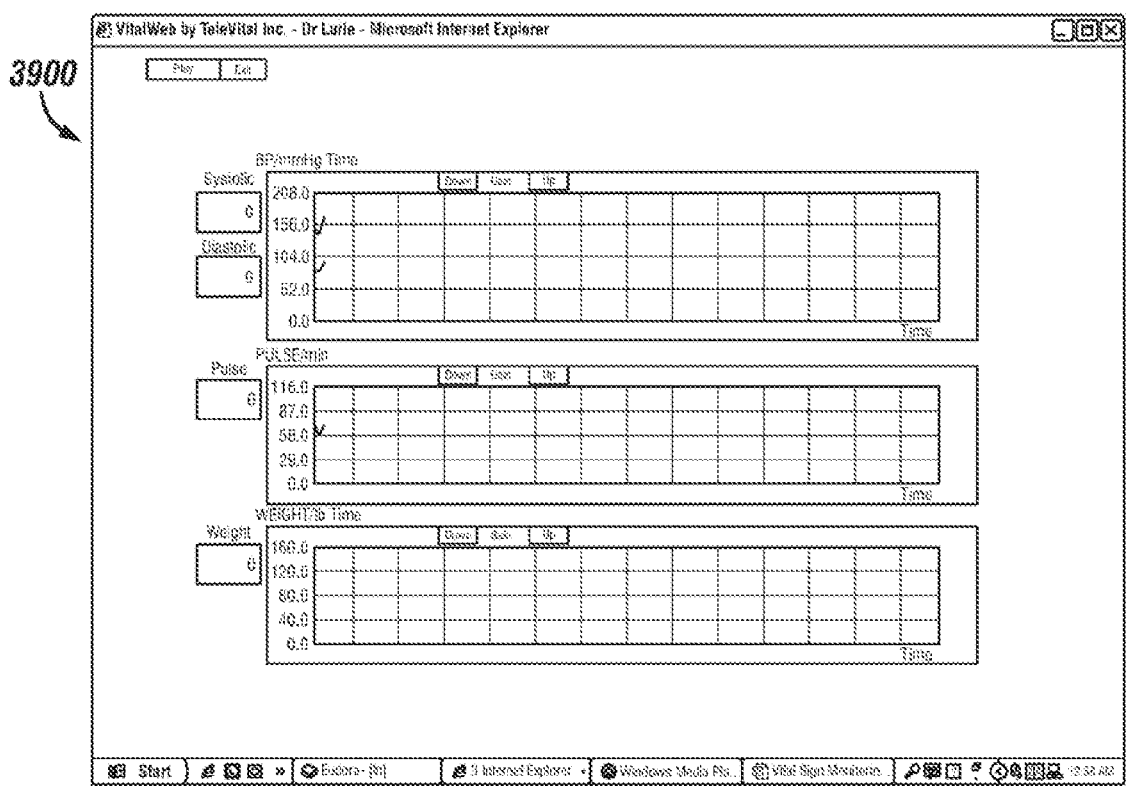
FIG. 39 shows an exemplary screen displaying weight and blood pressure monitoring data.

FIGS. 35 and 36 show illustrative screens 3500, 3600 displaying blood sugar monitoring data. FIG. 37 depicts an exemplary screen 3700 displaying EMG monitoring data that can be used as part of a headache treatment protocol. FIG. 38 depicts an illustrative screen 3800 displaying peripheral body temperature data. FIG. 39 shows an exemplary screen 3900 displaying weight and blood pressure monitoring data.

Figure 40:
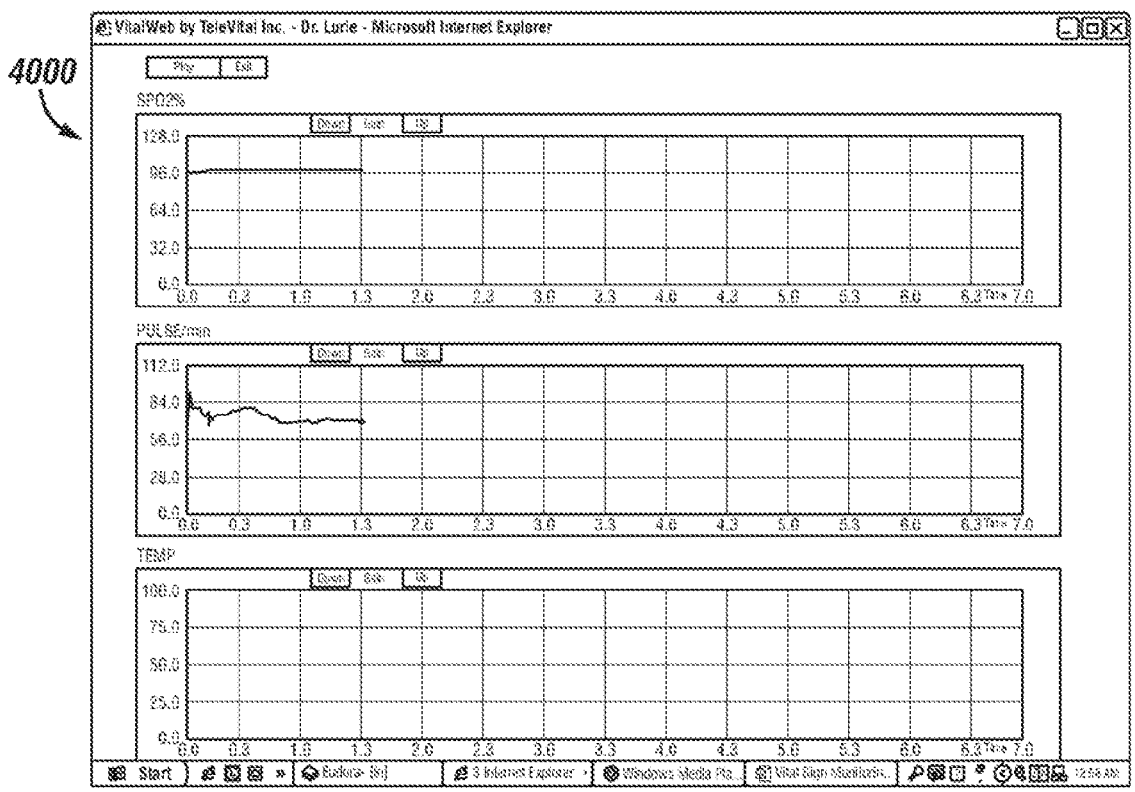
FIG. 40 illustrates an exemplary screen graphically displaying vital sign data.
Figure 41:
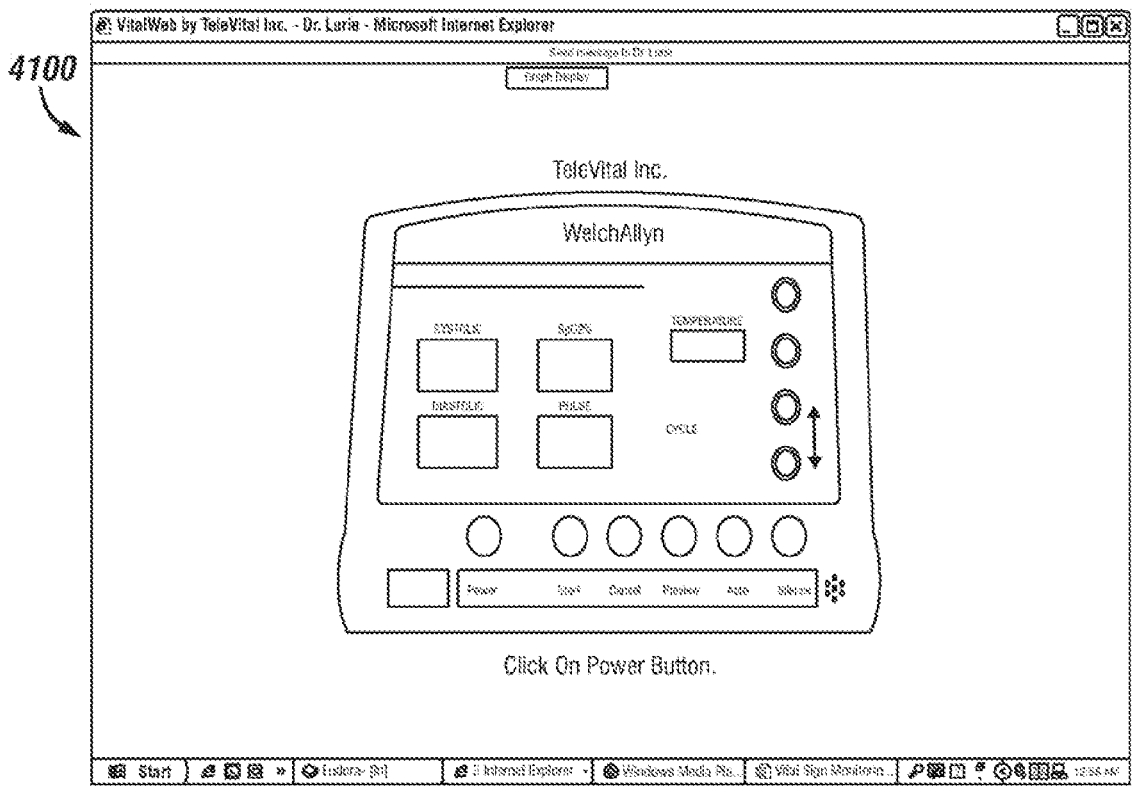
FIG. 41 depicts a screen showing another illustrative manner of displaying vital sign information, here by visually reproducing a client-side device.

FIG. 40 illustrates an exemplary screen 4000 graphically displaying vital sign data. FIG. 41 depicts a screen 4100 showing another illustrative manner of displaying vital sign information, here by visually reproducing a patient-side device and displaying the information that would be displayed on the patient-side device.

Remote fetal monitoring and monitoring of elderly patients can be conducted to remotely monitor for signs of trouble. This would provide peace of mind for parents, spouses, offspring, etc.

A further application includes monitoring patients on a mass scale. For example, such a using a screening protocol can include screening persons in third world countries on a large scale.

Revenue Models

Several revenue models are provided by the embodiments presented herein. For example, a fee may be charged for the creation and or acquisition of dedicated server software which includes an engine and one or more applications such as cardiology or pulmonology.

According to another embodiment, a fee may be charged for transmitting the data, storing the data, accessing the data, etc. For example, medical providers, device manufacturers, and service providers may pay a one-time (or continuing) development cost for web-enabling their devices or treatment protocols and supporting those devices/protocols in the engine. These uses may then resell the server software along with their hardware. In another example, these persons/entities may also be billed on a monthly basis per acutal online and streaming time.

Generally cardiologists cannot charge insurance when their patients call them over the phone complaining about their chest pain. With web-enabled devices, not only they can provide better services to their patients, but they can also charge the insurance for real-time interpretation of the ECG/event monitor signals. The system can be adapted to automate and web enable health provider protocols for ECG/pacemaker/ICD interpretations so that they can offer their protocols to other cardiologists for a fee.

In another revenue model, advertisements may be posted to a website for a fee. When a provider or patient logs in, the advertisement is displayed. Another embodiment includes a subscription-based (ASP) model with a web based central server, where users are billed based on the usage or monthly flat fees. A further embodiment While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system for network-based transmission of data from a patient-side physiological collecting device, comprising:
    at least one patient-side device for collecting physiological data from a patient, the patient-side device being operatively coupled to a wide area network;
    multiple provider-side devices coupled to the network, the at least one patient-side device sending the data to the provider-side devices;
    an engine coupled to the network and resident on a device intermediate the at least one patient-side device and the provider-side devices, the engine communicating with the at least one patient-side device and the provider-side devices, the engine managing transmission of the data from the patient-side device to the provider-side devices;
    wherein the data is monitored for an event, wherein an alert is output by at least one of the patient-side device and the provider-side devices upon occurrence of the event,
    wherein the at least one patient-side device encrypts the data prior to sending the data;
    wherein a fee is charged for coordinating the sending of the data to the provider-side devices,
    wherein the at least one patient-side device includes a browser-based interface for allowing the patient to send human language communications to the provider-side devices,
    wherein the provider-side devices each include a browser-based interface for allowing one or more providers to send human language communications to the patient-side device,
    wherein one or more providers is allowed to remotely control the at least one patient-side device,
    wherein at least one of the one or more providers is allowed to remotely control at least a portion of the browser based interface of the at least one patient-side device,
    wherein clinical notes are stored on the device intermediate the at least one patient-side device and the provider-side devices,
    wherein the at least one patient-side device automatically detects medical devices coupled thereto.

2. The system as recited in claim 1, further comprising logic for predicting future behaviors and physiological responses of the patient based on the physiological data collected from the patient.

3. A system for network-based transmission of data from a patient-side physiological collecting device, comprising:
    at least one patient-side device for collecting physiological data from a patient, the patient-side device being operatively coupled to a wide area network;
    multiple provider-side devices coupled to the network, the at least one patient-side device sending the data to the provider-side devices;
    an engine coupled to the network and resident on a device intermediate the at least one patient-side device and the provider-side devices, the engine communicating with the at least one patient-side device and the provider-side devices, the engine managing transmission of the data from the patient-side device to the provider-side devices;
    wherein the data is monitored for an event, wherein an alert is output by at least one of the patient-side device and the provider-side devices upon occurrence of the event,
    wherein the at least one patient-side device encrypts the data prior to sending the data;
    wherein a fee is charged for coordinating the sending of the data to the provider-side devices,
    wherein a fee is charged by a human provider viewing the data on one of the provider-side devices,
    wherein the at least one patient-side device includes a browser-based interface for allowing the patient to send human language communications to the provider-side devices,
    wherein the provider-side devices each include a browser-based interface for allowing one or more providers to send human language communications to the patient-side device,
    wherein at least one of the one or more providers is allowed to remotely control the at least one patient-side device,
    wherein at least one of the one or more providers is allowed to remotely control at least a portion of the browser based interface of the at least one patient-side device,
    wherein clinical notes are stored on the device intermediate the at least one patient-side device and the provider-side devices,
    wherein the at least one patient-side device automatically detects medical devices coupled thereto.

4. The system as recited in claim 3, wherein the provider-side devices are wireless telephones having a wireless connection to the wide area network.

5. A system for network-based transmission of data from a patient-side physiological collecting device, comprising:
- at least one patient-side device for collecting physiological data from a patient, the patient-side device being operatively coupled to a wide area network;
- multiple provider-side devices coupled to the network, the at least one patient-side device sending the data to the provider-side devices;
- an engine coupled to the network and resident on a device intermediate the at least one patient-side device and the provider-side devices, the engine communicating with the at least one patient-side device and the provider-side devices, the engine managing transmission of the data from the patient-side device to the provider-side devices;
- wherein the data is monitored for an event, wherein an alert is output by at least one of the patient-side device and the provider-side devices upon occurrence of the event,
- wherein the at least one patient-side device encrypts the data prior to sending the data;
- wherein the at least one patient-side device compresses the data prior to sending the data;
- wherein a fee is charged for coordinating the sending of the data to the provider-side devices,
- wherein the at least one patient-side device includes a browser-based interface for allowing the patient to send human language communications to the provider-side devices,
- wherein the provider-side devices each include a browser-based interface for allowing one or more providers to send human language communications to the patient-side device,
- wherein at least one of the one or more providers is allowed to remotely control the at least one patient-side device,
- wherein at least one of the one or more providers is allowed to remotely control at least a portion of the browser based interface of the at least one patient-side device,
- wherein clinical notes are stored on the device intermediate the at least one patient-side device and the provider-side devices,
- wherein the at least one patient-side device automatically detects medical devices coupled thereto.

6. The system as recited in claim 5, wherein the patient-side devices and the provider-side devices support plug-and-play web device drivers and customized graphical user interfaces.

\* \* \* \* \*